(12) United States Patent
McCulloch et al.

(10) Patent No.: US 10,739,210 B2
(45) Date of Patent: Aug. 11, 2020

(54) SENSOR, CONTROLLER AND SYSTEM

(71) Applicant: Oxford University Innovation Limited, Oxford (GB)

(72) Inventors: Malcolm Duncan McCulloch, Oxford (GB); Peter Michael Armstrong, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 372 days.

(21) Appl. No.: 14/649,898

(22) PCT Filed: Dec. 4, 2013

(86) PCT No.: PCT/GB2013/053208
§ 371 (c)(1),
(2) Date: Jun. 4, 2015

(87) PCT Pub. No.: WO2014/087162
PCT Pub. Date: Jun. 12, 2014

(65) Prior Publication Data
US 2015/0323391 A1 Nov. 12, 2015

(30) Foreign Application Priority Data

Dec. 4, 2012 (GB) .................................. 1221828.5

(51) Int. Cl.
*G01K 7/00* (2006.01)
*G01K 7/22* (2006.01)
(Continued)

(52) U.S. Cl.
CPC ............ *G01K 7/22* (2013.01); *F24H 9/2007* (2013.01); *G01K 1/143* (2013.01); *G01K 13/02* (2013.01);
(Continued)

(58) Field of Classification Search
CPC combination set(s) only.
See application file for complete search history.

(56) References Cited

U.S. PATENT DOCUMENTS

| | | | | | |
|---|---|---|---|---|---|
| 4,686,998 A | * | 8/1987 | Robbins | ............... | A61B 5/0006 128/903 |
| 4,878,226 A | * | 10/1989 | McQuoid | ............... | G01K 1/026 374/166 |

(Continued)

FOREIGN PATENT DOCUMENTS

| | | |
|---|---|---|
| EP | 2233858 | 9/2010 |
| GB | 588729 A | 6/1947 |

(Continued)

OTHER PUBLICATIONS

English translation of EP2233858.*

(Continued)

*Primary Examiner* — Lisa M Caputo
*Assistant Examiner* — Nasir U. Ahmed
(74) *Attorney, Agent, or Firm* — Schwegman Lundberg & Woessner, P.A.

(57) ABSTRACT

The present invention relates to a sensor for measuring temperature of a fluid within a vessel, the vessel having a first region and a second region and the fluid having a temperature profile extending between the first region and the second region, the sensor comprising an array of elements, each element having a temperature-dependent parameter, the array being capable of deployment within or adjacent the vessel such that the array extends along the vessel for measuring the temperature profile, the elements of the array being coupled together between an input and an output, the input being coupled or capable of being coupled to a driving source for driving the sensors, and the output being coupled or capable of being coupled to a detector for measuring an aggregate of the temperature-dependent (Continued)

parameter from the array of elements. The invention further relates to a fluid temperature controller comprising a first input for receiving a first signal indicating a measurement of an aggregate of a temperature-dependent parameter from a sensor according to any preceding claim deployed within or adjacent a vessel containing a fluid having a temperature profile, a second input for receiving a second signal indicating a (preferably absolute) temperature of the fluid in the vessel and a processor configured to calculate a total thermal energy of the fluid in the vessel based on the first and second signals. The invention also relates to a combination comprising a sensing arrangement and a controller; a device; and a system.

20 Claims, 10 Drawing Sheets

(51) Int. Cl.
| | |
|---|---|
| *G01N 25/00* | (2006.01) |
| *G01N 33/18* | (2006.01) |
| *G01N 33/00* | (2006.01) |
| *G01K 1/14* | (2006.01) |
| *F24H 9/20* | (2006.01) |
| *G01K 13/02* | (2006.01) |
| *G05D 23/19* | (2006.01) |
| *F24D 19/10* | (2006.01) |

(52) U.S. Cl.
CPC ......... *G01N 25/00* (2013.01); *G01N 33/0004* (2013.01); *G01N 33/18* (2013.01); *G05D 23/1931* (2013.01); *F24D 19/10* (2013.01); *F24D 2220/042* (2013.01); *F24D 2240/26* (2013.01); *G01K 2013/026* (2013.01); *G01K 2213/00* (2013.01)

(56) References Cited

U.S. PATENT DOCUMENTS

| | | | | |
|---|---|---|---|---|
| 5,435,188 A | * | 7/1995 | Lew | G01F 1/125 73/861.22 |
| 6,959,599 B2 | * | 11/2005 | Feldstein | G01F 23/246 340/622 |
| 7,262,360 B1 | * | 8/2007 | Davis | B63H 19/00 136/201 |
| 2001/0040159 A1 | * | 11/2001 | Jirmann | B60H 1/00428 219/480 |
| 2007/0096287 A1 | * | 5/2007 | Araki | H01L 25/105 257/686 |
| 2009/0160405 A1 | * | 6/2009 | Takeda | H01M 10/0525 320/152 |
| 2010/0088410 A1 | * | 4/2010 | Ridley | H04L 41/0896 709/224 |
| 2011/0157755 A1 | * | 6/2011 | Honkura | H01M 10/4235 361/93.8 |
| 2011/0211612 A1 | * | 9/2011 | Branecky | F24D 19/1006 374/115 |
| 2012/0024240 A1 | * | 2/2012 | Beckley | F24H 1/18 122/14.2 |

FOREIGN PATENT DOCUMENTS

| | | |
|---|---|---|
| GB | 2051370 A | 1/1981 |
| GB | 2192988 A | 1/1988 |
| JP | 61-211666 A | 9/1986 |
| JP | 04-050740 A | 2/1992 |
| JP | 2006125709 | 5/2006 |
| WO | WO-88/05160 A1 | 7/1988 |
| WO | WO-2011/103447 A1 | 8/2011 |
| WO | WO-2014/087162 | 6/2014 |

OTHER PUBLICATIONS

A. Barzegar and A.A. Dehghan "Transient Thermal Behavior of a Vertical Solar Storage Tank with a Mantle Heat Exchanger during No-Flow Operation", Journal of Applied Fluid Mechanics, vol. 2, No. 1, pp. 55369, 2009.*
NPL (Wayback Machine Capture of "Thermocouple" from Wikipedia), Nov. 14, 2012.*
"International Application No. PCT/GB2013/053208, International Preliminary Report on Patentability dated Jun. 9, 2015", 11 pgs.
"United Kingdom Application No. GB1221828.5, Search Report dated Apr. 5, 2013", 7 pgs.
"International Application No. PCT/GB2013/053208, International Search Report and Written Opinion dated May 20, 2014", (May 20, 2014), 17 pgs.
"New Zealand Application No. 709702, First Examination Report dated Sep. 8, 2017", (Sep. 8, 2017), 5 pgs.

* cited by examiner

SENSOR, CONTROLLER AND SYSTEM

PRIORITY CLAIM TO RELATED APPLICATIONS

This application is a U.S. national stage application filed under 35 U.S.C. § 371 from International Application Serial No. PCT/GB2013/053208, which was filed 4 Dec. 2013, and published as WO 2014/087162 on 12 Jun. 2014, and which claims priority to United Kingdom Application No. GB1221828.5, filed 4 Dec. 2012, which applications and publication are incorporated by reference as if reproduced herein and made a part hereof in their entirety, and the benefit of priority of each of which is claimed herein.

The present invention relates to a sensor for measuring temperature of a fluid within a vessel, as well as to a related fluid temperature controller and system. In particular, the invention relates to a sensing and control arrangement for a liquid or gas heating or cooling system. The sensing arrangement is used to determine volumes of heating fluid/coolant at or above/below a predetermined useful temperature. The controller may refer changes to thermal inputs or outputs based on the output of the sensor and determined useful volume of fluid.

There are numerous instances where a volume of fluid is stored for heating applications with end-use temperature requirements such as domestic hot water provision, space heating or cleaning. In many such applications it is useful to know how much thermal energy there is along with the associated temperature distribution. In the case of domestic hot water, knowing the temperature distribution throughout the vertical extent of the reservoir enables one to compute the useful volume of fluid according to Equation 1, $$V_{useful} = \int_{y(T_{thresh})}^{h} A(y)\left[1 + \frac{T(y) - T_{thresh}}{T_{thresh} - T_c}\right]dy, \quad (1)$$

where $V_{useful}$ is the volume of mixed fluid from a mixed outlet, A is the horizontal cross-sectional area of the fluid storage vessel containing a stratified body of fluid some of which exists at a temperature above $T_{thresh}$ beneath which the fluid is too cold for direct use, for example as a hot water source. T(y) is the temperature distribution along a (typically horizontal) y-axis within the vessel with height h. The temperature of the fluid at an inlet of the vessel is denoted by $T_c$. The mixed fluid is delivered from a mixing valve which takes a flow of fluid from a cold inlet and hot outlet. The temperature distribution needs to be measured for the purposes of the above calculation. The threshold temperature, $T_{thresh}$, may often be associated with the thermocline within a stratified body of fluid. A thermocline is an abrupt temperature gradient in a body of water, the layer above having a different temperature from the layer below. The position of the thermocline can be used to infer the quantity of available hot water, in the case of the hot water forming a distinct top layer. The thermocline can be used to determine the useful potential associated with a quantity of thermal energy.

Cooling with heat exchange temperature requirements, such as cold storage, is often used in refrigeration and air-conditioning applications. A vessel containing chilled brine may be used in an industrial process which requires removal of waste heat. Within a stratified vessel of cold fluid, such as brine, the useful or cooling potential of fluid, defined as the volume of coolant, $V_{useful\ (cooling)}$ or waste heat brought to a threshold temperature, is expressed by Equation 2, $$V_{useful\ (cooling)} = \int_{y=0}^{y(T_{thresh})} A\left[\frac{T(y) - T_{thresh}}{T_{thresh} - T_h}\right]dy, \quad (2)$$

where $T_{thresh}$ refers to the desired temperature below which is waste heat in the system, T(y) is the temperature distribution throughout the stored coolant, A is the cross-sectional area of the vessel and $T_h$ is the initial temperature of the fluid to be cooled. Equation 2 applies to a vessel of water stored above the transition temperature associated with a change in correlation between water density and temperature for a particular operating pressure, typically 2-6° C., or more preferably 3-5° C., at 0.25-2 bar, or more preferably at 0.75-1.25 bars.

Knowing the useful heating or cooling volume can enable determination of the approximate position of the thermocline within the vessel. Where a tank contains hot water for potable or bathing applications, temperatures beneath the lowest heating point are often insufficient to ensure full sterilisation of human pathogens such as *Pseudomonas, Legionella, E. coli*, etc. This situation arises due to the fact that conductive heat transfer through water in a tank is significantly slower than the rate of convective heat transfer that arises above an immersion element or heat exchanger. Since this leads to a portion of water within a tank that may host pathogens, a risk arises to the user whenever the tank is drained past the thermocline position (for example the shower going cold when the hot water runs out) as the user may then be exposed to unsanitary water. A system which monitors the position of the thermocline can therefore make the user aware of both the available volume of hot water along with the risk of exposure to unsanitary water. Furthermore, such a system can intervene to minimise such risks by ensuring that the distance between the hot water tank outlet and thermocline is kept above a minimum distance at all times in dependence of the usage profile of the system.

There are a number of sensors that attempt to monitor the thermal energy content within a vessel.

One such example comprises a mechanical water level sensing arrangement operating alongside a means of measuring the electricity consumption of a heating element. However, a mechanical approach is compromised by moving parts, fouling and cost.

An alternative comprises a single thermistor detector. Single temperature measurement may provide an indication of a full tank. However, ignorance of a temperature distribution throughout a vessel prevents a user from determining the remaining quantity of useful heat or cooling potential.

A further alternative comprises a plurality of temperature sensors. A plurality of temperature sensors results in a compromise between the accuracy of measurement (governed by number density of temperature sensors) and the cost and complexity associated with monitoring multiple channels simultaneously.

Further still, an alternative sensor comprises a resistive strip made up of a string of thermistors. A string of Positive Temperature Coefficient (PTC) or Negative Temperature Coefficient (NTC) thermistors can resolve the average temperature within a vessel. However, knowing only the average temperature within the vessel is insufficient in determining the useful volume above a particular threshold temperature. Furthermore, the response of a PTC string is non-linear resulting in large error compared with an ideal response. A string of NTCs is not well suited to resolve the lower limit of the integral in Equation 1 and 2, resulting in a lack of knowledge of the threshold temperature above which useful energy (also referred to as exergy) content exists.

According to the present invention, there is provided a sensor for measuring temperature of a fluid within a vessel, the vessel having a first region (such as adjacent a fluid inlet) and a second region (such as adjacent a fluid outlet) and the fluid having a temperature profile extending between the first region and the second region, the sensor comprising an array of elements, each element having a temperature-dependent parameter, the array being capable of deployment in association with (typically within or adjacent) the vessel such that the array extends along the vessel for measuring the temperature profile, the elements of the array being coupled together between an input and an output, the input being coupled (or capable of being coupled) to a driving source for driving the sensor(s), and the output being coupled (or capable of being coupled) to a detector for measuring an aggregate of the temperature-dependent parameter from the array of elements.

Further features of the invention are characterised by the dependent claims.

Preferably, the elements of the array are coupled in a chain.

Preferably, an aggregate value of the temperature-dependent parameter is indicative of thermal energy content of the fluid in the vessel.

Preferably, the aggregate value of the temperature-dependent parameter has a predetermined relationship to the thermal energy content of the fluid in the vessel.

Preferably, at least one of the elements of the array is configured such that the temperature-dependence of the temperature-dependent parameter is at or near a maximum or minimum at or near a temperature that is a threshold temperature between a useful temperature of the fluid and a non-useful temperature of the fluid.

The temperature-dependent parameter may be resistance, impedance, inductance and/or capacitance.

The elements of the array may be coupled together in series or parallel.

The elements of the array may comprise at least one thermistor.

At least one of the elements of the array may comprise a Positive Temperature Coefficient resistor and/or a Negative Temperature Coefficient resistor and/or a fixed value resistor.

At least one of the elements of the array may comprise a fixed value resistor connected in parallel with a Positive Temperature Coefficient resistor and/or a fixed value resistor connected in parallel with a Negative Temperature Coefficient resistor.

At least one of the elements of the array may comprise a Positive Temperature Coefficient resistor connected in parallel with a Negative Temperature Coefficient resistor and in series thereto a fixed value resistor.

Preferably, the Positive Temperature Coefficient resistor and/or Negative Temperature Coefficient resistor is a non-linear resistor.

The elements of the array may comprise at least one electronic filter circuit, including, but not exclusive to, RC, RL and RLC circuits. Preferably, each element of the array has a predetermined and unique cut-off frequency, preferably at a pre-determined temperature.

Preferably, the sensor is arranged such that selective interrogation of elements of the array can be achieved by exploiting (or using), the unique cut-off frequency of the elements of the array, preferably to determine an interrogated cut-off frequency. Preferably the sensor is arranged to be selectively interrogated by the driving source by applying a frequency sweep around the unique cut-off frequency.

Preferably, the sensor is arranged such that selective interrogation of elements of the array comprises finding an interrogated cut-off frequency or measurement of a temperature dependent parameter.

Preferably, the selective interrogation of elements of the array comprises finding an interrogated cut-off frequency wherein the temperature-dependent parameter is the interrogated cut-off frequency and wherein the relationship between the predetermined cut-off frequency and interrogated cut-off frequency is used to determine a measure of temperature.

Preferably, the relationship between predetermined and interrogated cut-off frequency is indicative of a temperature.

Preferably, the temperature dependent resistance of a thermistor is indicative of a temperature.

The elements of the array may comprise at least one RLC circuit. Preferably, each element of the array has a predetermined and unique resonant frequency, preferably at a predetermined, temperature and the sensor is arranged to find the resonant frequency.

Preferably, the sensor is arranged to be selectively interrogated in order to find an interrogated resonant frequency of interrogate elements of the array to find the resonant frequency. Preferably the relationship between predetermined and interrogated resonant frequency is indicative of a temperature.

Preferably, the relationship between predetermined and interrogated resonant frequency is indicative of a temperature.

Preferably, the relationship between predetermined and interrogated resonant frequency, indicative of temperature, further indicates the thermal energy content of the fluid in the vessel.

Preferably, the detector is arranged to derive the thermal energy content of the fluid in the vessel from the relationship between the predetermined and interrogated resonant frequencies.

The elements of the array may comprise at least one semiconducting device.

Preferably, the semiconducting device element of the array is biasable to enable manipulation of the threshold temperature.

Preferably, the array comprises a substrate that can be cut to length to determine the number of elements within the array. A substrate can provide support and enable manipulation of the array so as to enable cutting.

Preferably, the substrate comprises a pipe. A pipe can provide a simple and economical substrate that shelters and protects the array and provides support.

Preferably, the substrate comprises an adhesive tape. This can enable fixation of the array to a vessel wall. Alternatively, the substrate may comprise a flexible strip or flexible circuit board.

Preferably, the sensor is arranged within a vessel or externally to the vessel.

The elements of the array may be non-uniformly distributed along the length of the sensor array according to sensing requirements.

According to a further aspect of the invention, there is provided a sensing arrangement comprising a sensor (optionally according to the above description), and at least one thermometer, the sensor and said at least one thermometer having a shared output.

Preferably, the sensor and said at least one thermometer are coupled together such that there are only two output connectors for the shared output.

Preferably, the sensor and said at least one thermometer are arranged in parallel.

Preferably, the sensor comprises means for measuring an output from the thermometer separately to the output from the sensor.

Preferably, the thermometer monitors the temperature adjacent the vessel outlet or inlet to detect when fluid is at an unsanitary temperature;

Preferably, the output of the at least one thermometer is used to determine the useful volume of fluid within the vessel and/or calibrate the output of the sensor. Preferably, the at least one thermometer is used to measure the temperature of fluid at an inlet of the vessel in order to determine or improve the estimate of the useful volume of fluid associated with a predetermined threshold temperature. Preferably, the temperature of fluid at an outlet, measured by the at least one thermometer, allows identification of unsanitary exposures and provides a calibration reference from the sensor; hence a record can be made where fluid is at an unsanitary temperature, for example a temperature of less than 70° C., 60° C., or, more preferably, less than 50° C.

Preferably, the detector comprises a means of adjusting the output of the sensor in dependence of the output of the thermometer, preferably according to Equation 1; hence the accuracy of the sensor is correlated to the thermometer, thereby improving accuracy of the sensor output or vice versa.

Preferably the thermometer is arranged to normalize the output of the sensor, in order to improve accuracy of the sensor.

According to another aspect of the invention there is provided a fluid temperature controller comprising a first input for receiving a first signal indicating a measurement of an aggregate of a temperature-dependent parameter from a sensor, preferably comprising an array of elements that have a temperature-dependent parameter, deployed within or adjacent a vessel containing a fluid having a temperature profile, a second input for receiving a second signal, optionally from a thermometer as described above, indicating a temperature, preferably an absolute temperature, of the fluid in the vessel, preferably adjacent the location of the thermometer, and a processor configured to calculate a total thermal energy of the fluid in the vessel based on the first and second signals.

The fluid temperature controller may be further configured to determine a volume of useful fluid in the vessel further based on a predetermined threshold temperature between a useful temperature of the fluid and a non-useful temperature of the fluid.

Preferably, the processor is further configured to provide an output control signal for controlling a thermal source that changes the temperature of the fluid in the vessel. The fluid temperature controller may be further configured to determine an appropriate timing for the output control signal based on timing patterns of at least the first signal. Preferably, the fluid temperature controller is arranged to provide the output control signal to the thermal source based on historical variations of at least the first signal.

Preferably, the processor is further configured to account for any number of array elements and/or array element spacing along the length of the sensor. Preferably, the processor is configured to operate in dependence upon the number of array elements and/or array element spacing along the length of the sensor.

The fluid temperature controller may comprise a network stress monitor, the network stress monitor being arranged preferably to receive data from a network operator and to modify the output control signal to a heating element or the thermal source, preferably in dependence of the data received from the network operator, to optimise the timing of dispatch of thermal energy. This can enable a heating element controller to regulate power consumption so as to take advantage of supply peaks in the supply network, and avoid supply troughs in the supply network. This can provide a supply balancing effect to the supplier and a cost benefit to the user.

Preferably, the network stress monitor modifies the output control signal to the heating element or thermal source in dependence on the supply network voltage and/or grid current frequency.

Preferably, the network stress monitor modifies the output control signal to the heating element or thermal source in dependence on data from a network operator. A sensor as described above may provide the first signal.

According to a further aspect of the invention, there is provided a combination comprising a sensing arrangement (optionally as described above) and a controller arranged to process the shared output from the sensing arrangement, wherein the sensing arrangement and/or controller is arranged to determine signals from the sensor and at least one thermometer separately and to compute the useful quantity of thermal energy within a vessel containing a fluid.

Preferably, the combination is arranged to determine signals from the sensor and thermometer separately by impedance isolation of the thermometer.

Preferably, the combination is arranged to determine signals from the sensor and thermometer separately by using alternating current and direct current Preferably, the combination comprises multiple thermometers, preferably in conjunction with network of thermistors.

Preferably the sensing arrangement is arranged to indicate if the amount of fluid within the vessel above the unsanitary temperature, as described above, falls below a predetermined threshold.

According to yet a further aspect of the invention, there is provided a device for identifying removal of fluid from a vessel, comprising: means (such as an input) for receiving an output from a sensor, the output relating to a thermal property of the fluid within the vessel, and a processor arranged to identify removal of the fluid from the vessel in dependence on a rate of change of the output from the sensor and a predetermined threshold value of the output. By identifying removal of fluid from the vessel, usage of fluid of fluid can be logged.

Preferably, the threshold is arranged to be equal to or greater than static heat loss from the vessel; preventing changes in output from the sensor from being interpreted as removal of fluid from the vessel.

Preferably, the device comprises an output for outputting an instruction to induce a temperature change in the fluid within the vessel when the device identifies removal of fluid from the vessel.

Preferably, the processor has an input arranged to indicate when a temperature change is being induced in the fluid, the processor being arranged to modify the rate of change of the output from the sensor so as to cancel/mitigate the effects of the induced temperature change in the fluid to identify removal of fluid from the vessel. Preferably, the device is arranged to isolate effects to the rate of change of the output from the sensor due to activity from the thermal source, preferably by receiving information regarding scheduled times of activity of the thermal source. Preferably, the device is arranged to factor-in any contribution from a heat source or thermal source so that the change in a useful volume of fluid due to removal of fluid from the vessel can be decoupled from the total change in sensor output whilst a simultaneous heating event occurs. Preferably, the device is arranged to monitor changes in the output of the sensor for the purpose of dis-aggregating draw and heating events, or measures identified as removal of fluid from the vessel, from the continuous change due to standing heat losses. Preferably, with knowledge of the heat source timing and controller of the heat source is also able to decouple a draw event when simultaneous heating occurs. Preferably, the useful volume of fluid due to removal of fluid can be isolated or decoupled from the total change in output from the sensor, preferably while the thermal source is active.

According to another aspect of the invention, there is provided a system comprising a device (optionally as described above), said sensor and said vessel, the sensor being located adjacent an outlet of the vessel.

According to another aspect of the invention, there is provided a device for measuring temperature of a fluid within a vessel, the device comprising: a sensor (optionally as described above) for determining a thermal property of a fluid within a vessel, wherein the sensor is arranged to be fitted onto an exterior wall of the vessel; and a processor for receiving the output from the sensor and adjusting the output according to thermal properties of the wall of the vessel. Thereby, the accuracy of the output from a sensor arranged to infer thermal properties of a fluid through a vessel wall may be improved.

Preferably, said sensor comprises an array of elements, each element being adapted to determine a thermal property at a different location on the vessel.

Preferably, wherein the processor uses a model of the wall of the vessel.

According to another aspect of the invention there is provided a device for measuring temperature of a fluid within a vessel, the device comprising: a sensor (optionally as described above), for determining a useful volume of a fluid within a vessel, wherein the sensor is arranged to be fitted onto an exterior wall of the vessel; and a processor for receiving an output from the sensor and adjusting the output from the sensor in dependence upon changes induced in the fluid by a thermal source or the influence of the thermal source on a useful volume of fluid within the vessel.

The invention extends to a system comprising a vessel, the vessel having a first region (such as adjacent a fluid inlet) and a second region (such as adjacent a fluid outlet) and the fluid having a temperature profile extending between the first region and the second region, a sensor or a sensing arrangement (optionally as described above) and a fluid temperature controller (optionally as described above).

The fluid in the system may be gas or liquid.

The system may comprise a vessel that is a hot water tank, a fluid that is water and a threshold temperature comprising a temperature beneath which the water is too cold or not useful, for example, below a temperature of 60° C., 50° C., 40° C. or 30° C., for direct use as hot water.

The system may comprise a vessel that is a coolant tank, a fluid that is a coolant and a threshold temperature comprising a temperature beneath which the fluid is too hot for direct use as a coolant.

The invention extends to a sensor, controller, device and system, substantially as herein described with reference to the accompanying figures.

According to another aspect of the invention there is provided a controller arranged to interpret the signal from a thermocline sensor (optionally as described above) and, on the basis of that signal, compute the useful quantity of thermal energy within a vessel containing a liquid.

Preferably, the controller is capable of modulating the timing and quantities of any thermal inputs or outputs from a vessel containing a liquid on the basis of a user requirement and thermocline position measurement derived from a thermocline sensor as described in this document.

Preferably, the controller can track cyclical patterns of signal output from a thermocline sensor within a vessel containing a liquid, or preferably externally to the vessel, and on this basis optimise the dispatch of thermal energy using any other additional parameters such as user input, user requirement, energy cost, distribution network voltage and/or grid frequency and in the case of domestic hot water systems, sanitary requirements.

Preferably, the controller can provide a user with an indication of the useful volume of thermal energy on the basis of the signal produced by a thermocline sensor.

Preferably, the thermocline sensor's output signal is combined with one or more temperature signals to provide a reference to a controller within which the useful quantity of energy is computed.

Preferably, the thermocline sensor is physically immersed within a vessel containing a fluid or is in physical contact with the wall of a vessel, preferably on an interior or exterior wall of the vessel, containing a liquid so that the temperature distribution and associated useful quantity of thermal energy within the liquid can be inferred.

Preferably, the thermocline sensor comprises a number of temperature measuring elements whose outputs are aggregated in such a way as to provide one or more signals that describe the useful quantity of thermal energy within a vessel.

Preferably, the thermocline sensor comprises of a number of resistive elements exhibiting a fixed value or negative or positive relationship with temperature.

Preferably, the thermocline sensor's total network resistance is a function of the quantity of energy and temperature distribution within a liquid stored in a vessel.

Preferably, the thermocline sensor's resistive elements are connected in a series or parallel arrangement.

Preferably, the thermocline sensor comprises of an arrangement of individual Thermocline Edge Detectors (TEDs) further comprising of positive or negative coefficient thermistors in parallel with another resistive element such as a fixed value resistor.

Preferably, the thermocline sensor comprises any number of TEDs arranged in a series or parallel configuration.

Preferably, the TEDs are designed to abruptly change in resistance according to the passing of a thermocline within a body of stratified liquid within a vessel.

Preferably, the TEDs response is achieved through the selection of the Curie transition temperature associated with a positive temperature coefficient thermistor.

Preferably, the accuracy of the TEDs and resistance-to-useful volume relationship is optimised via addition of parallel or series negative temperature coefficient or positive temperature coefficient thermistors, resistors or any other resistive element.

Preferably, the thermocline sensor's network resistance values are determined by any means, such as voltage measurement associated with a known current; current measurement associated with a known voltage, timing of current change in or voltage change across an inductor or capacitor connected to or within resistive network.

Preferably, the thermocline sensor comprises of a number of reactive elements exhibiting some dependence on temperature.

Preferably, the thermocline sensor or TEDs comprises a temperature reference sensor for inferring useful volume delivered to an end user.

Preferably, the thermocline sensor or TEDs comprise a temperature reference sensor for monitoring a hot outlet of the vessel to record potentially unsanitary exposures to hot water, for example less than 60° C., 50° C., 40° C. or 30° C. Preferably, an inlet temperature reference from the temperature reference can be used to improve the estimate of useable volume through application of Equation 1.

Preferably, the controller is capable of measuring the impedance of a thermocline sensor in order to compute the useful volume of thermal energy within a vessel filled with a liquid using any impedance measurement technique, such as, but not limited to, frequency magnitude and/or phase response and/or impulse response test from some arbitrary input waveform to reactive network.

Preferably the controller is arranged to apply a wall heat flux function, preferably applied to a resistive thermal model to correct measures of temperature of the vessel wall in order to determine the temperature of the fluid within the vessel.

Preferably, the controller comprises means, such as a processor, of mapping a wall heat flux function for the temperature and temperature gradient of the external vessel wall to an empirical or computed relationship between a wall position and heat flux, wherein a simplified function is parameterized on the basis of features, for example thermal parameters, of the vessel wall, temperature measures of the vessel wall and the temperature gradient.

Preferably, the wall heat flux function further comprises a model for adjusting for the effects of thermal transient effects associated with fluid flow, heat capacitance and conduction to the ambient environment of the vessel and fluid.

Preferably, the controller comprises a processor for mapping a temperature profile of the vessel wall and/or fluid within the vessel, to an output from a thermal source for a given flow rate and temperature of an inlet of the vessel. Preferably, the processor is arranged to apply a model of the thermal source to a one-dimensional or two-dimensional model of the fluid within the vessel, preferably for modelling the stratification of the fluid, in order to resolve or determine a change in the rate of change of temperature of fluid adjacent to the outlet of the vessel, for a given flow rate of fluid into or out of the vessel for a given temperature adjacent the inlet of the vessel. Preferably, the processor is arranged to determine the useful volume of energy or mass of hot water above a predetermined useful temperature.

Preferably, the controller comprises a device for identify removal of fluid from the vessel in dependence of the rate of change in output from the thermocline sensor or a temperature sensor array. Preferably, the controller is arranged to output an instruction to activate a thermal source in dependence of identification of removal of fluid from the vessel. Preferably, the processor is arranged to use machine learning to instruct the thermal source. Preferably, the processor is arranged to determine if the volume of useful fluid within the vessel is below a predetermined threshold. Preferably, the processor is arranged to indicate to a user if volume of useful fluid within the vessel is below a predetermined threshold.

The invention extends to methods and/or apparatus substantially as herein described with reference to the accompanying drawings.

Any apparatus feature as described herein may also be provided as a method feature, and vice versa. As used herein, means plus function features may be expressed alternatively in terms of their corresponding structure, such as a suitably programmed processor and associated memory.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

These and other aspects of the present invention will become apparent from the following exemplary embodiments that are described with reference to the following figures in which:

FIG. 1 shows a fluid storage vessel annotated to show the schematic communication between a sensor, fluid temperature controller, heating element and fluid outlet;

FIG. 2 *a*) shows a sensor-fluid outlet pipe interface for horizontal outlet connections;

FIG. 2 *b*) shows a sensor-fluid outlet pipe interface for vertical outlet connections;

FIG. 3 *a*) shows a sensor comprising of Thermocline Edge Detectors (TEDs) in series;

FIG. 3 *b*) shows a sensor comprising of Thermocline Edge Detectors (TEDs) in parallel;

FIG. 4 *a*) is a circuit diagram of a sensor with TEDs in series;

FIG. 4 *b*) is a circuit diagram of a sensor with TEDs in parallel;

Figure 1:
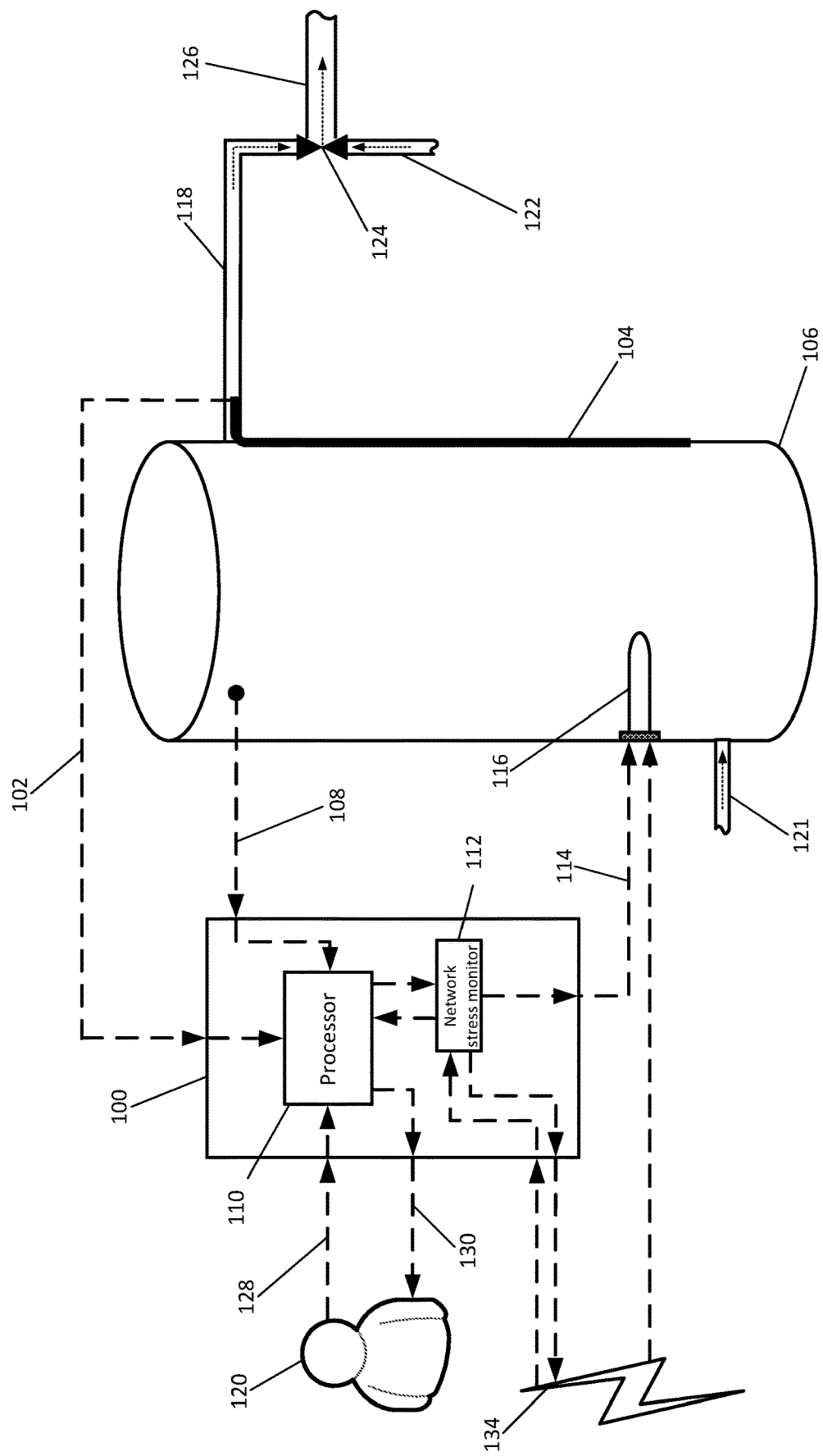

FIG. 1 shows a fluid temperature controller 100 comprising a first input for receiving a first signal 102 indicating a measurement of an aggregate of a temperature-dependent parameter from a sensor 104 within or adjacent a vessel 106 (for example, on an interior or exterior wall of the vessel) containing a fluid, either liquid or gas, having a temperature profile. The fluid temperature controller 100 has a second input for receiving a second signal 108 indicating a temperature of the fluid in the vessel. A processor 110 in communication with the controller is configured to calculate thermal energy of the fluid in the vessel based on the first and second signals. A linear exergy sensor is therefore provided.

The processor 110 is further configured to determine a volume of useful fluid in the vessel based on the first signal 102 and second signal 108 and a predetermined threshold temperature between a useful temperature of the fluid and a non-useful temperature of the fluid. The processor of the controller computes the useful volume of fluid available in the vessel 106. The computation by the processor can be according to an equation similar in form to Equation 1 or 2. If the sensor 104 performs according the Equation 1 or 2, then the processor can apply signal conditioning to compute the useful volume of fluid available in the vessel 106. The sensor 104 is therefore a linear exergy sensor and the linear exergy sensor provides a signal that provides weight to the useful energy above the threshold temperature (rather than a binary indication beyond a useful temperature).

The processor 110 is configured to provide an output control signal to the controller 100, which in turn produces an output 114 that regulates a thermal source 116 (e.g. a heating element in the case of an electric system) so as to change the temperature of the fluid in the vessel. The controller determines whether the proximity of the thermocline to the vessel outlet 118 is such that there is an insufficient useful amount of volume of fluid and thus a risk of a user 120 being exposed to fluid which is at an insufficient temperature. Furthermore, the controller aims to prevent a user from being exposed to pathogenic bacteria that could dwell beneath the lowest thermal injection point (in the illustrated example the thermal source 116), whilst at the same time minimising standing heat losses. If such sanitary risks arise on a regular basis, the controller 100 can arrange for additional thermal energy to be added as a preventative measure in advance.

The fluid proceeds along the fluid outlet 118 whereupon it is mixed with fluid from a cold inlet 122, the output of which is regulated by a mixing valve 124, and the fluid emerges in a mixed outlet 126. The fluid in the vessel 106 is replenished through a cold inlet 121. A temperature profile extends between the cold (inlet) region in the vessel 106 and the hot (outlet) region in the vessel 118. The temperature profile may exhibit a distinct thermocline, or it may exhibit a gradual transition.

The output control signal that the processor 110 provides to the controller 100 is subject to approval from or adaptation by a network stress monitor 112. The network stress monitor 112 can modify the output control signal in dependence on factors that relate to the network stress. For example, the supply voltage, supply frequency data, or data communications from the supply provider 134 can provide information relating to the network stress. Optionally or alternatively the controller 100 can interact with the supply provider 134 to affect dispatch of energy based on network stress information, and so enable dispatch of energy to the vessel according to availability of energy in the vessel and the cost of energy.

The processor 110 can relate cyclic changes in output from the sensor 104, for example over a 24-hour period, to determine, in addition to other parameters such as energy costs, user input 128, user 120 requirements, the optimal timing associated with any thermal inputs or outputs from a vessel 106 containing a fluid, distribution in network voltage and/or grid frequency as determined by the network stress monitor 112. An adaptive Markov model, or similar statistical approach, could run on the controller and adjust probability weightings assigned to future draw events based on previous draw events and their associations with particular activities (for example the probability of a shower within an hour after a user has drawn a bath) along with the time of day. The Markov model predicts the most likely future demand to allow an algorithm to establish the optimal dispatch of power to immersion elements. A machine-learning process is used to optimally schedule heating of fluid within the vessel according to use of the fluid in the vessel.

The fluid temperature controller 100 is able to output information 130 regarding the quantity of fluid above (in the case of hot fluid applications) a useful temperature in addition to its mixing potential to the user 120.

The signal from the sensor 104 is supplemented by an additional temperature sensing input to yield absolute temperature readings 108 in order to normalize the response of the sensor during cyclical operation.

In one embodiment, the sensor 104 is immersed within the fluid inside the vessel 106. The sensor 104 can be in contact with the vessel wall 200, hence providing an indication of the temperature distribution. In this case, the sensor 104 can be fixed to the inner or outer surface of the vessel wall 200.

Figure 2:
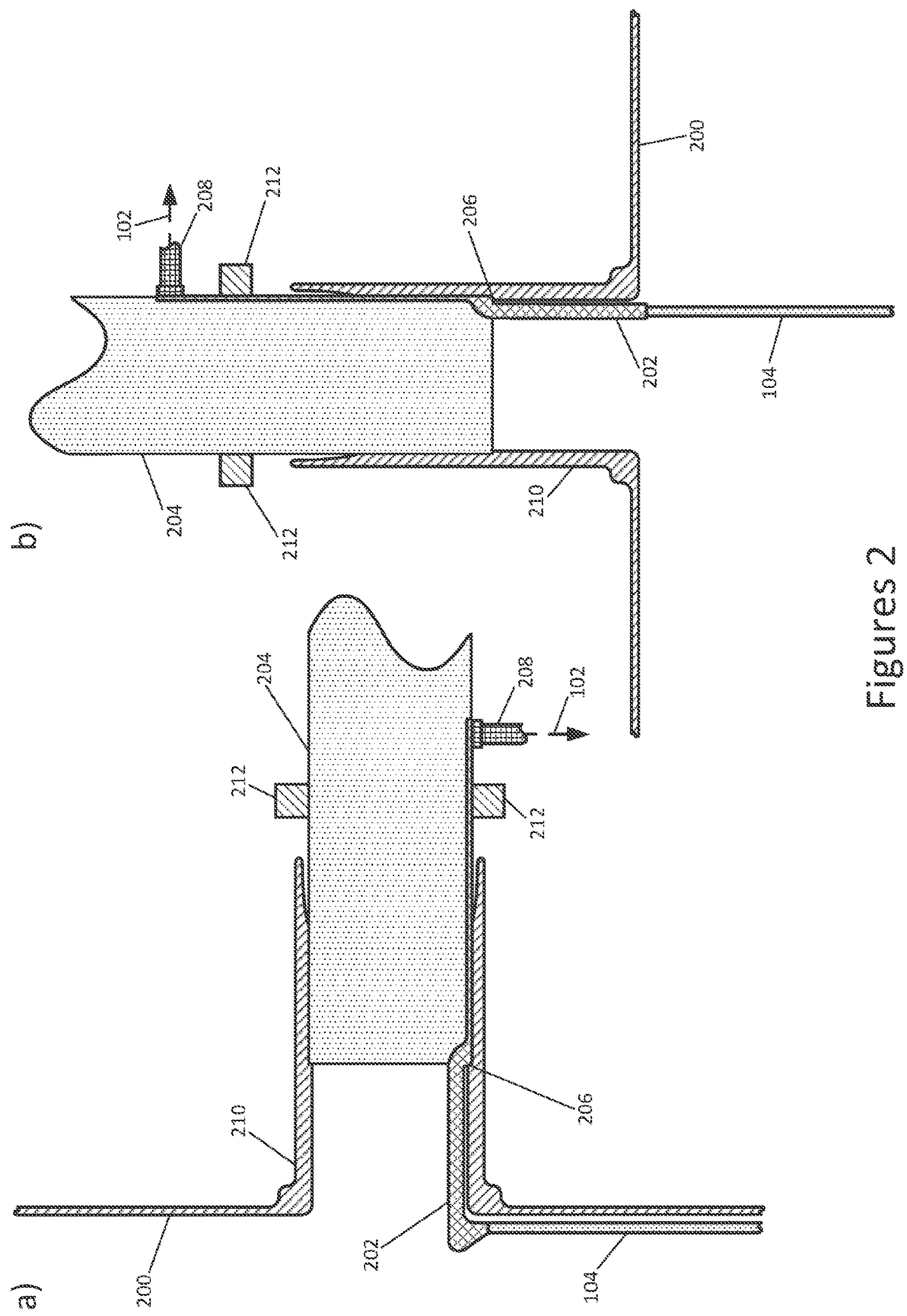

FIG. 2a illustrates a mechanical arrangement whereby a protrusion from a sensor-pipe interface 202 from a section of pipe 204 clears (via an optional step) the flange recess shoulder 206. For vessels with horizontal outlet connections, the protrusion 202 bends through 90° before continuing down towards the bottom or up towards the top of the vessel. The circuitry associated with the sensor is embedded in the sensor strip 104. The wiring associated with the sensor is embedded in the sensor strip, protrusion 202 and pipe 204 wall prior to emerging as the connecting wire 208 carrying the sensor output 102. The wire 208 terminates at a suitable connector, for example, a two or more pinned connector. The sensor-pipe interface 202 connects to the tank flange 210 and fluid distribution system via compression, push-fit, bolted flange or any other appropriate arrangement 212. FIG. 2b illustrates a mechanical arrangement for vessels with vertical connections. The sensor 104 protrudes vertically from the sensor-pipe interface 202 into the vessel, with no bend. FIGS. 2a and 2b show ¾ inch British Standard Pipe (BSP) external threaded compression fittings, which are exemplary fittings that are commonly found in UK domestic hot water systems.

Figure 3:
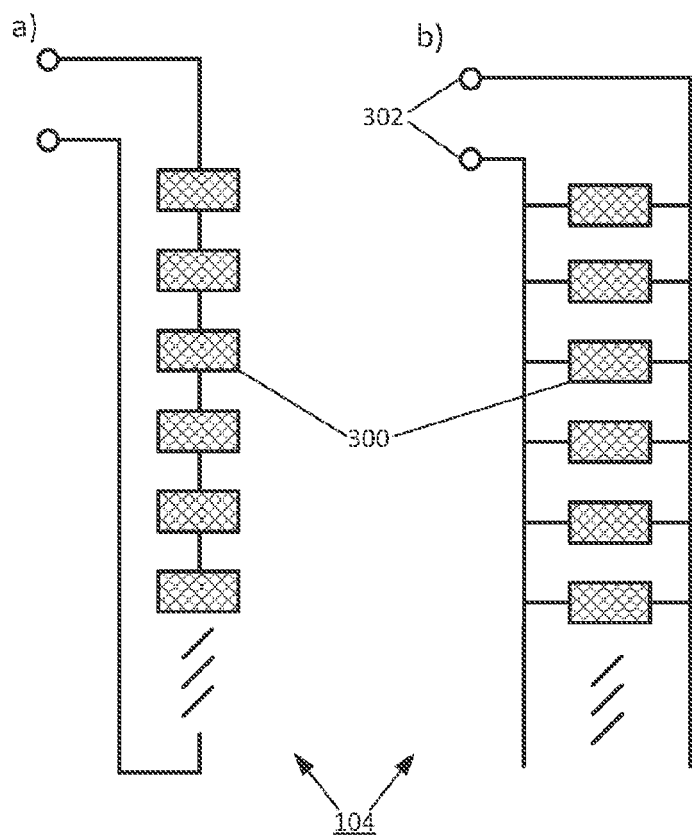

FIGS. 3a and 3b show sensors 104 with Thermocline Edge Detectors (TEDs) 300. Each TED 300 is an element in an array of similar elements. In FIG. 3a TEDs 300 are connected in series. In FIG. 3b TEDs 300 are connected in parallel, where the individual TEDs 300 can act as shunts. The TEDs 300 are such that the sensor's temperature response follows Equation 1 or 2 (whether or not a temperature profile exhibits a thermocline). The TEDs 300 have a temperature-dependent parameter that gives rise to a temperature response, e.g. changes in resistance or AC impedance. The resistance, impedance or rise time for a temperature-dependent RC network is inferred by: applying a fixed voltage across the sensor terminals; applying a known frequency across the sensor electric terminals 302; injecting a known current through the sensor; or monitoring the response to an impulse or any other arbitrary input function of current or voltage over time. A measure of impedance is made at terminals 302; this is achieved by wiring the network to a fixed resistor with known reference voltage and recording the voltage across the terminals 302 as in a voltage divider circuit, or through measurement of a voltage drop on application of a known constant current.

Any number of TEDs 300 can be arranged in a series or parallel chain to provide indication of the total thermal energy in the vessel. The positioning and spacing of the TEDs 300 within the sensor strip 104 can vary according to sensing requirements. For example, a higher resolution is required close to the vessel outlet 118 to determine thermocline position with greater accuracy and thus potential sanitary risk to a system user.

Whilst independent wiring of TEDs 300, PTC thermistor or NTC thermistor arrays provides the most accurate resolution of useful volume, this approach also requires multiple electrical connections and channels within the signal conditioning arrangement. The sensors 104 described here require a single measurement channel reducing cost and complexity whilst improving reliability. The linear exergy sensor therefore feeds one signal to the control unit from the network of thermosensitive elements. In addition, for the output of sensors wherein resistance is exploited as the temperature-dependent parameter used to indicate useful volumes of fluid, only gain and bias requirements are imposed on signal conditioning, whereas some form of numerical integration of the output of an independent array is required for the same purpose increasing the complexity of any algorithm making the measurement.

Figure 4:
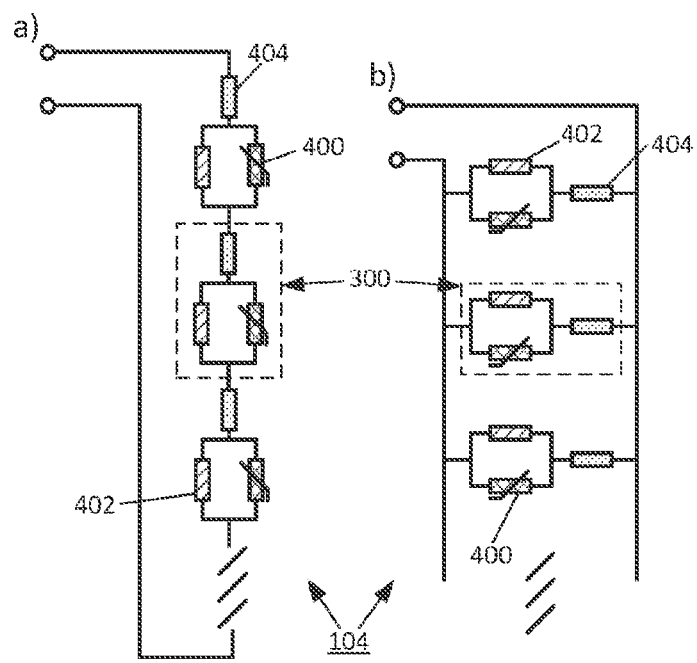

FIG. 4a shows a circuit diagram of a sensor 104 comprised of an array of TEDs 300 connected in series. FIG. 4b shows a sensor 104 with an array of the same TEDs 300 as FIG. 4a, but with the TEDs 300 connected in parallel. Each illustrated TED 300 comprises three elements: a thermistor 400 in parallel to a resistive element 402 and in series thereto a resistor 404. The elements within a TED 300 can act as shunts. The thermistor 400 can be a PTC or NTC thermistor. The resistive element 402 is shown as a resistor, but it can alternatively be a PTC or NTC thermistor or another resistive element. The resistor 404 can be omitted.

The resistance of networks such as in FIGS. 4a and 4b is inferred via current measurement with constant voltage or voltage measurement with constant current. The current drawn by the sensor for a fixed voltage corresponds to an aggregate of temperature-dependent resistance of the TEDs, which corresponds with the useful volume once the appropriate signal conditioning has been applied. The aggregated temperature-dependent resistance is a cumulative summation of the resistance of the elements (or a selection of the elements) of the sensor array.

Figure 5:
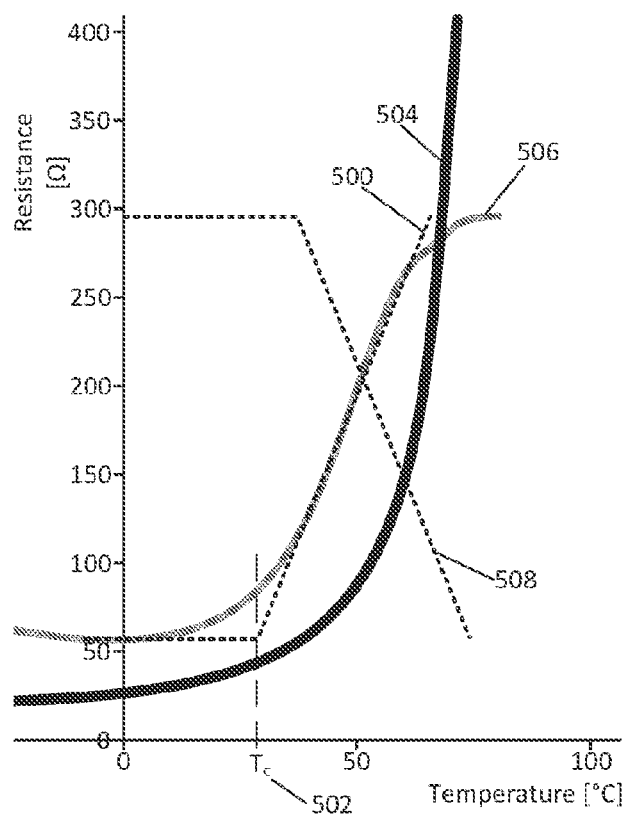
FIG. 5 shows the temperature dependence of the resistance of a TED.

FIG. 5 shows the temperature dependence of the resistance of a TED. The ideal resistance curve 500 (dashed line) represents an ideal TED with constant resistance up until the Curie temperature 502 of the thermistor; above the Curie temperature 502, the resistance increases linearly with temperature. A typical resistance curve 504 (black solid line) of a real-world thermistor is not linear, nor is there a distinct transfer from a constant-resistance regime to a linear-increasing regime. A TED circuit designed to approximate the ideal resistance curve 500 has a PTC thermistor in parallel with a fixed value resistor. The TED circuit curve 506 (grey solid line) of this circuit behaves significantly more closely to the ideal curve 500 than does the thermistor on its own (typical thermistor curve 504). For a TED with an NTC thermistor an ideal resistance curve 508 (dashed line) is also shown, and the typical real-world thermistor resistance curve and TED circuit curve are analogous to the illustrated PTC curves. For applications where an upper threshold temperature is relevant (in addition to the lower threshold of the Curie temperature 502 as described above), a curve with an upper temperature threshold, after which the resistance remains constant again, can be implemented, analogous to the illustrated curves.

The sensor 104 in FIG. 4a, comprising a chain of TEDs 300 connected in series, applied to determining the useful volume of hot fluid within a vessel, solves Equation 1 numerically by scaling and biasing the change in terminal resistance of the thermocline sensor according to Equation 3, $$\int_{y(T_{thresh})}^{h} A(y)\left[1 + \frac{T(y) - T_{thresh}}{T_{thresh} - T_c}\right] dy \approx K\left[\sum_{n=TED@T_{thresh}}^{N} R_{TED}(T)\right] - N\beta. \quad (3)$$

For a given TED, index n, the temperature-dependent resistance, represented by $R_{TED}(T)$, is only effective above the component's Curie temperature. Therefore, the cumulative resistance on the right-hand side of Equation 3 only includes temperature-dependence associated with TEDs immersed at a temperature above the Curie transition temperature. The Curie transition temperature is selected to coincide with the thermocline transition temperature of interest and thus sets $T_{thresh}$. For $T(y)<T_{thresh}$, $R_{TED}(T)\neq 0$, so the bias term, $N\beta$, is required, where N is the total number of TEDs and $\beta$ is the asymptote resistance for $R_{TED}$ ($T<T_{thresh}$). The gain term, K, scales $R_{TED}(T)$ back to $T(y)$ and in addition includes the term $A/T_{thresh}$. For the parallel arrangement of TEDs 300 shown in FIG. 4b, the useful volume of hot fluid within a vessel is solved by Equation 3 manipulated to account for the manner in which a parallel configuration of TEDs accumulates resistance. The thermistor elements provide an integral limit above a specified threshold temperature.

For determining a useful volume of coolant within a vessel, the sensors 104 illustrated in FIGS. 4a and 4b are comprised of TEDs where the thermistors 400 alternate along the sensor between PTC and NTC functionality. This arrangement numerically solves Equation 2 and can therefore be used to determine a useful volume of coolant below a threshold temperature. The sensor accuracy can be further improved by using an NTC thermistor parallel to a PTC thermistor instead of a fixed resistor parallel to a PTC or NTC thermistor.

An ideal TED responds to temperature transition across a threshold with an instantaneous transition from the temperature-independent regime to the temperature-dependent regime at a temperature associated with the thermocline transition temperature. In practice a TED may not display an abrupt change from the temperature-independent regime to the temperature-dependent regime, but instead displays a departure from the ideal function resulting in a function departure error. The presence of the parallel resistor 402 ensures that there is a linear response to temperature beyond the thermistor's Curie transition point. This helps create a more abrupt transition in resistance and manifests itself as a lower function departure error from the ideal function when the temperature of a particular section of the network crosses the threshold temperature. Without a parallel resistive element 402 the function departure error becomes very large and traverses a wide range of temperatures when compared with the response for a sensor inclusive of a resistive element 402 parallel to a PTC or NTC. Preferably a resistive element is connected in parallel to each TED to minimise the function departure error.

A benefit of a sensor comprising TEDs coupled in parallel is that any number of TEDs can be integrated into a strip which can be cut to the appropriate length or number of TEDs without loss of function to enable easy retrofit for a given installation. The controller 100 can be calibrated to a variety of sensor cut lengths either by having the corresponding response pre-programmed for a given length, or by normalizing the sensor output to a known reference state such as a fully heated or fully cold vessel of fluid.

The controller is capable of conditioning the resistance measurement such that a variable describing the quantity of useful energy remaining in a vessel is available. A parameter indicative of total thermal exergy within the vessel is therefore obtained.

Figure 6:
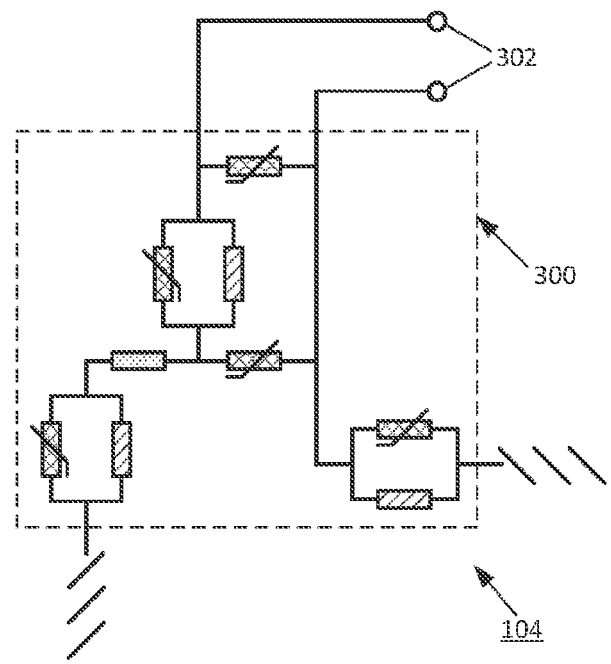
FIG. 6 is a circuit diagram of a further exemplary TED.

FIG. 6 illustrates a sensor comprising a further example of a resistive temperature reactive network 300 that solves Equation 1 or 2 for the purposes of determining the useful heating or cooling fluid volume within a vessel in a discretised manner with no more than two electrical terminals 302.

Figure 7:
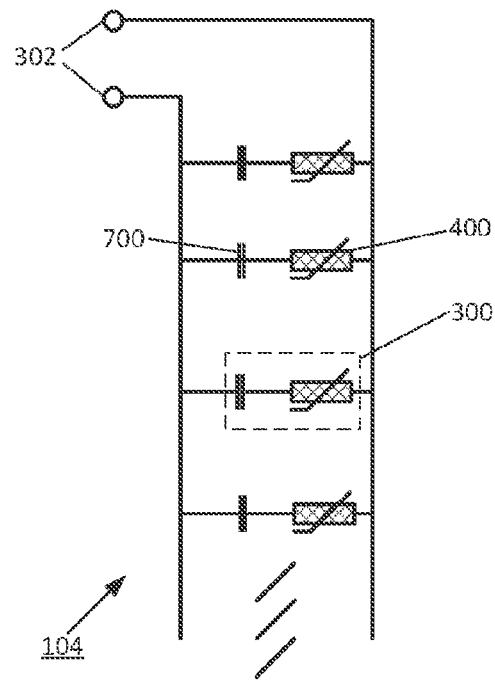
FIG. 7 is a circuit diagram of a sensor with RC-based TEDs.

FIG. 7 shows an alternative arrangement for a sensor 104 with a parallel arrangement of TEDs 300, each TED comprising a capacitor 700 in series with a temperature-dependent resistive element 400, thus forming an RC high-pass filter circuit. A sensor comprised of a serial configuration of RC-based TEDs is equally suitable. Throughout the TEDs in the sensor array, capacitors are selected to possess unique value capacitances, with the positions of particular unique value capacitances defined. Along the array identical NTC resistors are used. Therefore each TED possesses a unique predetermined cut-off frequency associated with the RC filter.

Selective interrogation of capacitive TEDs is achieved by driving the sensor with a sine wave signal at a low enough frequency such that the highest value capacitor (also associated with the RC circuit with the lowest cut-off frequency) behaves as a short circuit. The accompanying serial NTC thermistor's resistance governs the current drawn into the sensor array, which is proportional to the temperature of the thermistor. The signal from the remaining TEDs is not accounted since the input frequency is selected such that the remaining capacitors possess too little capacitance to admit current at this frequency and so appear as open circuits. The frequency is increased such that the second highest value capacitor behaves as a short circuit as the time constant associated with the RC circuit the capacitor comprises is encountered. Any change in current is associated with the temperature of the NTC resistor in series with the second highest value capacitor. The process is performed such that the remaining temperatures of the NTC thermistors in each TED are resolved in sequence allowing the temperature profile to be determined. The unique value capacitances can be arranged in an arbitrary sequence, provided the position of the individual capacitances is known. The process therefore utilises a frequency sweep in order selectively to interrogate elements of the array.

The same effect as described above for capacitive TEDs can be achieved with a sensor array comprising TEDs that more generally comprise electronic filters (each having a unique value) which are selectively interrogated within the array. Examples of suitable electronic filters include RL filters, low-pass filters, bandpass filters and any other similar arrangements.

Instead of measuring resistance at a particular frequency to determine a temperature-dependent parameter, as described above, The temperature at a given TED can also be gauged by determining the shift between predetermined cut-off frequency (that is, the cut-off frequency at a calibration temperature) and interrogated cut-off frequency (that is, the cut-off frequency at an actual, unknown, temperature to be measured). This allows the significant temperature-dependent parameter exhibited by some capacitors to be exploitable by having TEDs comprising fixed resistors in series with temperature-dependent capacitors. Each TED comprises an RC circuit with a unique predetermined cut-off frequency. The temperature at a given TED is inferred by selectively interrogating TEDs by manipulating input frequency and determining capacitance or the shift between interrogated and predetermined cut-off frequency. A temperature profile is thereby derived by accumulating the inferred temperature across the array.

Alternatively, an inductor can be introduced into the TEDs 300 shown in FIG. 7, thus forming an RLC circuit, which exhibits resonance. The RLC circuit of each TED 300 possesses a unique predetermined resonant frequency (via appropriate selection of fixed value resistors and/or NTC/PTC thermistors 400). The temperature associated with a particular RLC-based TED at a particular position is determined in isolation of other TEDs by applying a frequency across the sensor terminals 302 which is close to the predetermined resonant frequency associated with that particular TED. By modulating the applied frequency around the predetermined resonant point for that particular TED, the true resonant frequency can be found. The shift in resonant frequency exhibits a temperature-dependence from which temperature can be deduced. By interrogating the array in this manner, the temperature profile throughout the vessel can be deduced directly. The computation of Equation 1 or 2 is achieved via numerical integration of the resulting temperature profile.

Figure 8:
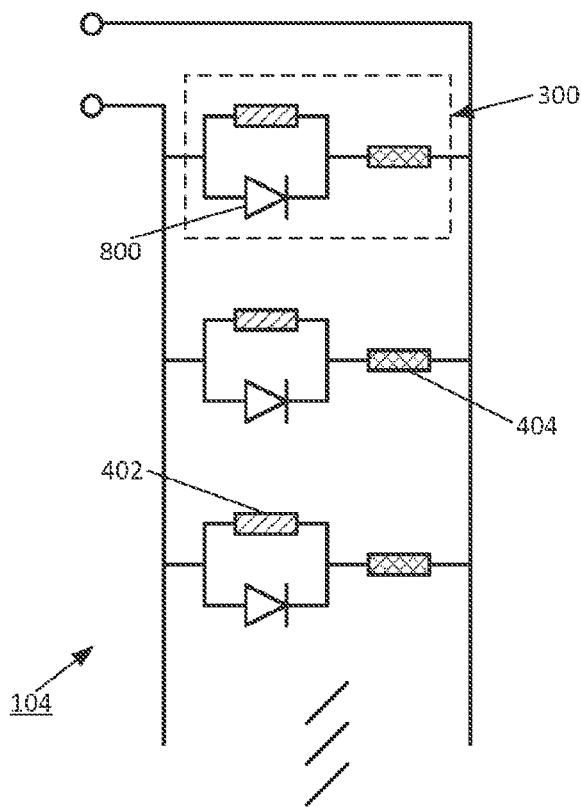
FIG. 8 is a circuit diagram of a sensor with diode-based TEDs.

FIG. 8 shows a TED 300 configuration comprised of diodes 800 parallel to resistive elements 402 and the combination in series with further resistive elements 404. Multiple TEDs 300 are connected in parallel to form a sensor 104. The TEDs can act as shunts in the parallel arrangement. Diodes exhibit temperature-dependent phenomena with respect to forward operating, reverse breakdown and current leakage performance characteristics. The current drawn by the sensor for a fixed voltage corresponds to an aggregate of temperature-dependent parameter of the TEDs, which corresponds with the useful volume once the appropriate signal conditioning has been applied. The leakage or reverse breakdown characteristics and their dependence on temperature are exploited by the series and parallel arrangements. Forward operating performance and its dependence on temperature can be exploited by reversing the orientation of all diodes 800. A sensor comprised of a serial configuration of diode-based TEDs 300 is equally suitable.

Figure 9:
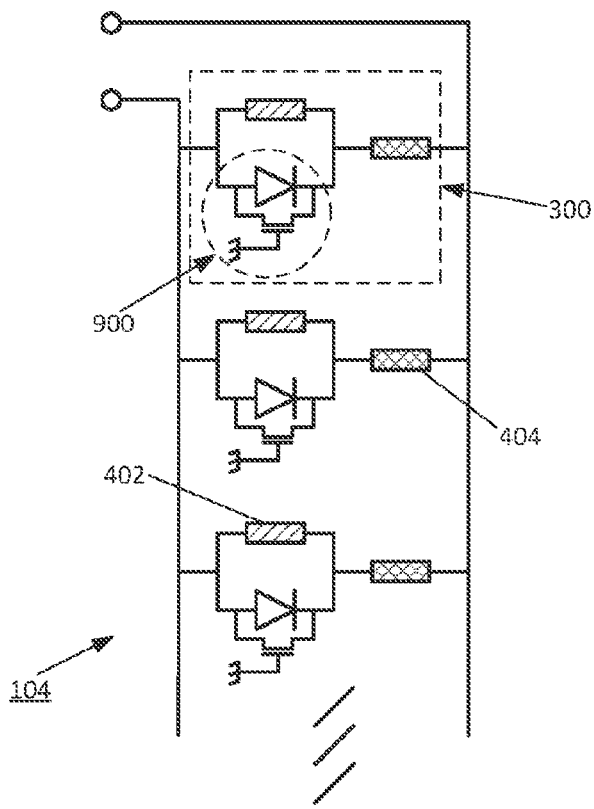
FIG. 9 is a circuit diagram of a sensor with grounded gate/base transistor-based TEDs.

FIG. 9 shows an arrangement of grounded gate/base transistor 900 TEDs 300 connected in parallel to resistive elements 402; in turn the combination is in series with further resistive elements 404. The TEDs 300 are connected in parallel to form a sensor 104. The parallel arrangement of TEDs forms a shunt circuit. There is a variety of transistor-based implementations that are conceivable including a number of bipolar and field effect approaches. Temperature-dependent phenomena associated with the intrinsic diode that exists between the collector/emitter or drain/source are exploited along with any leakage characteristics as discussed for diodes. A sensor comprised of a serial configuration of transistor-based TEDs 300 is equally suitable.

Figure 10:
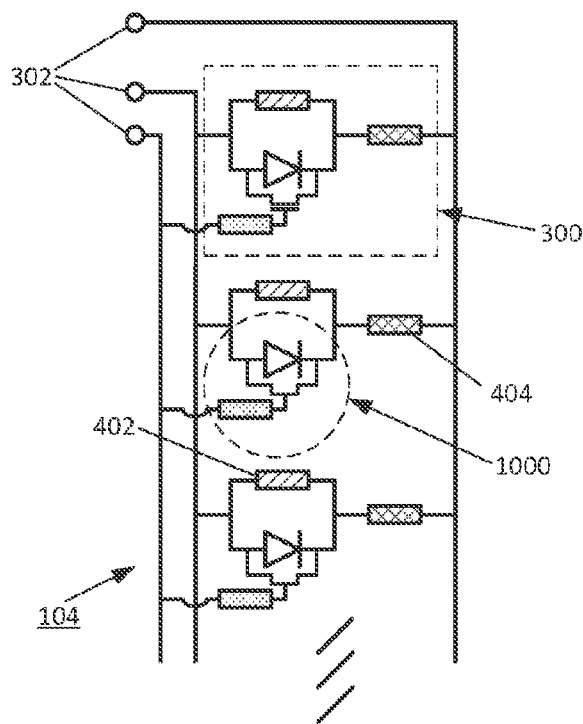
FIG. 10 is a circuit diagram of a sensor with biased gate/base transistor-based TEDs.

FIG. 10 shows an arrangement of biased gate/base transistor 1000 TEDs 300 connected in parallel to resistive elements 402, which combination is in series with further resistive elements 404. Reactive elements can be used in place of the resistive elements 402. The TEDs 300 are connected in parallel to form a sensor 104. The parallel arrangement of TEDs forms a shunt circuit. In the biased transistor 1000 instance, no more than three electrical terminals 302 are required to determine the useful heating or coolant fluid volume. The biasing facilitates control of the threshold temperature beyond which forward conduction takes place. The arrangements in FIGS. 8, 9 and 10 can be based around any type of semiconducting device such as field effect transistors, bipolar transistors, thyristors, etc. A sensor comprised of a serial configuration of biased-transistor-based TEDs 300 is equally suitable.

Figure 11:
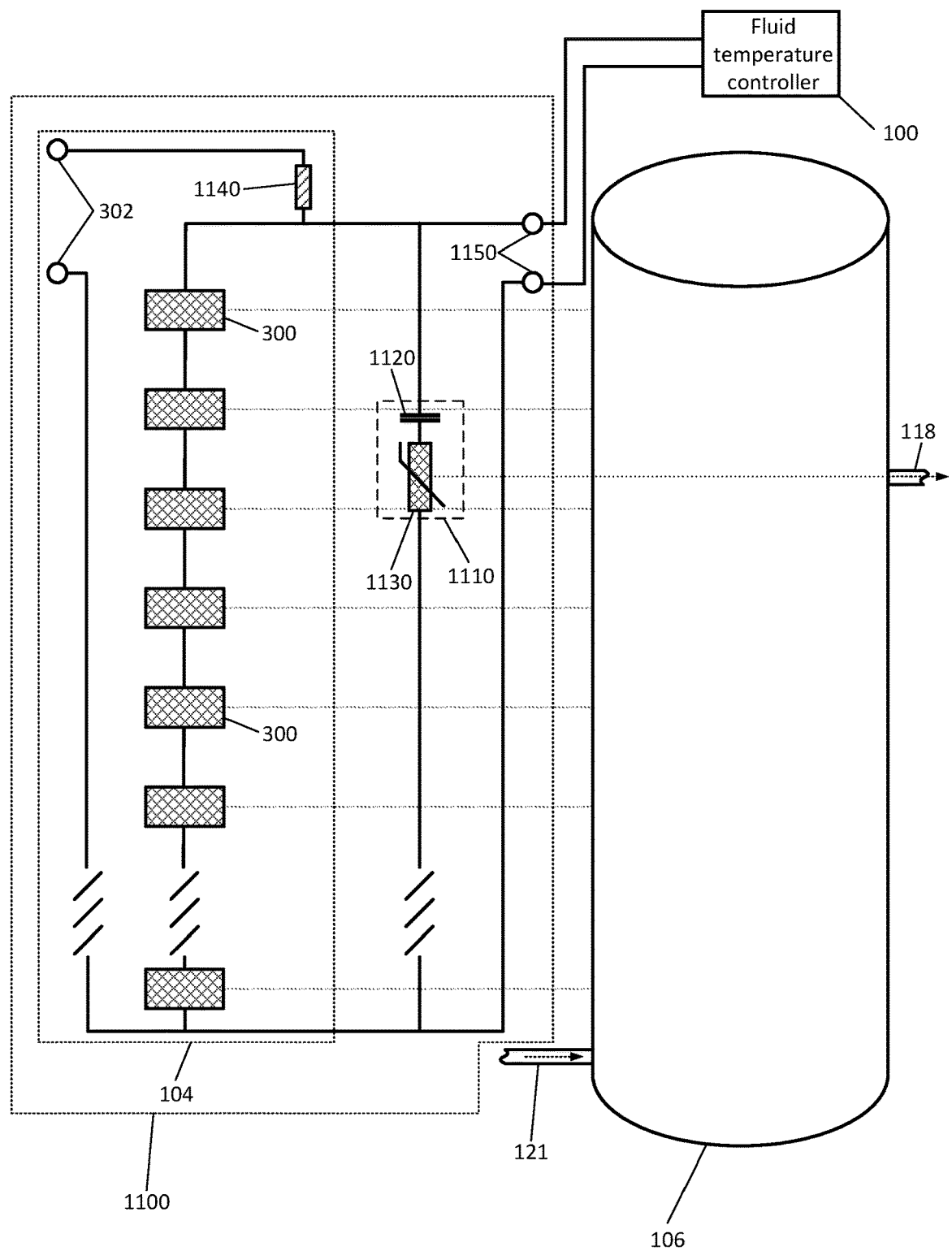
FIG. 11 is a schematic diagram of a thermocline sensor with an impedance isolated temperature sensor relative to a vessel.

FIG. 11 shows a circuit 1100 with a thermocline sensor 104 comprising an array of TEDs 300 (e.g. a shunt circuit with transistors or diodes—as described with reference to FIGS. 1 to 10) in parallel to a thermometer 1110 (as used herein, the term "thermometer" includes any form of temperature sensor, and as such does not necessarily actually provide a measurement of temperature). The thermometer 1110 is comprised of a thermistor 1130 (NTC or PTC), having a resistance $R_r$ in a serial arrangement with a capacitor 1120, with capacitance C. The arrangement of the circuit 1100 thereby allows a temperature reference from the thermometer 1110 to be determined separately to the output from the thermocline sensor 104, for example by using impedance isolation. Impedance isolation is, for example, afforded by the Resistor-Capacitor (RC) construction of the thermometer 1110 and by operating the circuit 1100 so as to exploit the filter properties of the RC thermometer. Alternatively, impedance isolation is achievable using a thermometer with an inductor, rather than capacitor (i.e. Resistor-Inductor). FIG. 11 shows a combination comprising a circuit 1100 and a controller 100, wherein isolating signals from the thermocline sensor 104 and thermometer 1110 is achieved by the controller and/or arrangement of the circuit 1100 and its components.

A signal indicative of the useable volume of water in the vessel 106 is obtained on application of a Direct Current (DC) signal—according to the response from the thermocline sensor 104—and a signal indicative of temperature at the point of the thermometer 1110 on application of an Alternating Current (AC) signal. The thermometer 1110 also allows the signal of the thermocline sensor 104 to be normalized.

In the example shown, a single thermometer 1110 is located at a point aligned with the vessel outlet 118. TEDs 300 are placed within the vessel 106 or externally to the vessel. The thermometer 1110 provides a measure of temperature adjacent its position.

It is advantageous for the circuit 1100, in particular the thermocline sensor 104, to be fitted to an outside thermally conductive wall of the vessel 106, since this enables the circuit 1100 to be retrofit. However, for vessels 104 with highly conductive walls (such as thick, e.g. >1 mm-3 mm, and/or British Standard grade 1 Copper walls) a significant discrepancy between the internal water and external wall temperatures arises due to differences in heat transfer between the water within the vessel 104 and the vessel wall. The discrepancy—most significant when there is a thermocline with a steep temperature gradient across it—is observed as a blurring of the otherwise sharp thermocline temperature transition point when inferring internal water temperature from the vessel wall. The accuracy to which the thermocline position is determined from measures of thermal properties of the vessel wall is therefore adversely affected. A model (referred to as a "wall model" herein) is used to obviate the thermal effects on measurements from a sensor that measures the thermal properties of fluid within the vessel through the vessel wall. The temperature profile and/or thermal exergy content of the fluid within the vessel, is available to be inferred by a sensor, such as the thermocline sensor 104, on an external wall of an insulated vessel, more accurately than without accounting for the thermal effects of the vessel wall. In one example, the wall model allows a sensor to be located adjacent to a vessel wall when the vessel and sensor are assembled during original manufacturing (and not just retrofit); this allows the sensor to be fixed to the vessel and then the insulation applied over the top of the vessel and sensor. The wall model is adapted according to measurements from the thermometer 1150.

The wall model is based on the thermal dynamics of heat flux across the vessel wall due to a stratified body of water contained within the vessel and applying analytical and/or interpolative techniques (for example a numerical spline method) in order to obtain a solution. In one example, a wall heat flux function that maps the temperature and temperature gradient of the external wall of the vessel to an empirical or computed relationship between a position on the vessel wall and heat flux is used, and parameterization of such a function is used on the basis of features of the vessel wall temperature and temperature gradient.

More elaborate wall models, for example accounting for transient thermal conduction, are alternatively applied, wherein the influence of fluid flow within the vessel during operation, distributed heat capacitance and conduction to the ambient environment is considered so that the sensor is capable of accounting for these effects.

Knowledge of the thermal dynamics of the vessel and fluid, allows the output of the thermocline sensor 104 to be fit to a thermal model of the vessel and fluid. The accuracy of measurements from the thermocline sensor 104 is thereby maintained with fewer array elements, e.g. TEDs 300. For example, 4-12 array elements allows for the thermal energy of the fluid to be suitably determined using; more preferably 7-9 array elements are used, but no fewer than 2-4 array elements are used.

In an alternative example, a linear exergy sensor composed of independent individual sensors traversing strata of fluid within a vessel is used to obtain a temperature profile of the fluid. In one example, the independent array of sensors comprises at least one of: a thermistor, thermocouple and/or any of the thermocline sensors 104 described herein. A signal compressor is used to aggregate the outputs from the sensors in order to determine the position of the thermocline and thus the thermal exergy of the fluid. When the number of independent sensors is small, e.g. <2-5 independent sensors, the output of the independent sensors is fit to a thermal model in order to improve the accuracy of the temperature profile, for example using regressions or interpolation techniques (such as spline fitting).

Figure 12:
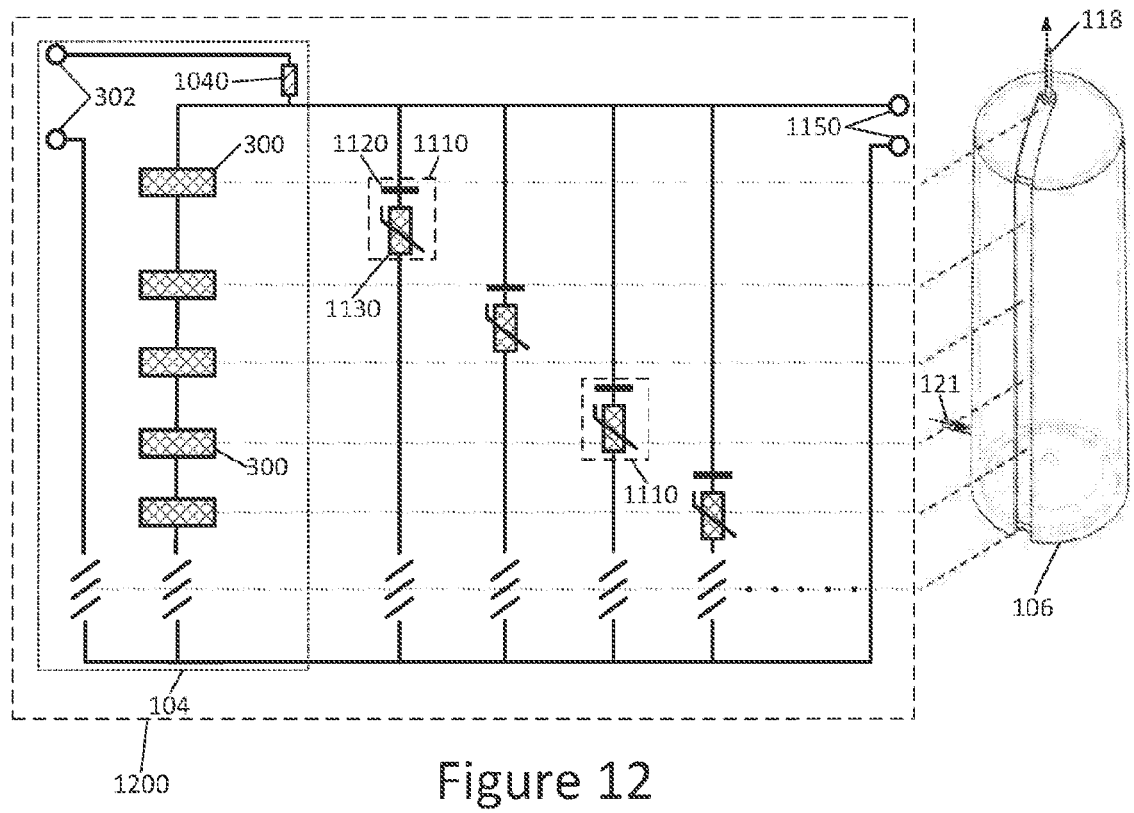
FIG. 12 is a further diagram of a thermocline sensor with multiple impedance isolated temperature sensors.

FIG. 12 shows an alternative circuit 1200 to the example shown in FIG. 11, whereby a plurality of thermometers 1110 are connected in parallel to the thermocline sensor 104 so as to traverse different positions of the vessel 106, for example the vessel outlet 118, inlet 121 and/or intermediate positions therein. In one example, the thermometers 1110 are distributed along the vessel at isochoric intervals. The low pass leg of the thermometer 1110 arrangement is replicated in the circuit 1200 introducing additional pole and/or zero time terms for multiple impedance isolated thermometers 1110 in different locations of the vessel 106. An array of impedance isolated thermometers 1110 allows individual temperature readings to be made for each thermometer 1110. A means of compiling a temperature profile of the fluid in the vessel is also achieved by independently interrogating each thermometer 1110 of such an array, and thereby aggregate a temperature profile of the fluid within the vessel.

The output of an array of thermometers 1150 is improved, when the array of thermometers is coupled with a sensor with finer resolution, such as a thermocline sensor 104 comprising a high number of PTC based TEDs 300.

The volume of useful fluid within the vessel is dependent upon both the temperature distribution throughout the tank (detected either by the thermocline sensor 104 or an array of thermometers 1110) along with the temperature of any cold water used for the purposes of mixing. Monitoring the temperature of the vessel inlet 121, for example using a thermometer 1110, and making the assumption that this is representative of inlet temperatures feeding appliances downstream of the vessel (e.g. the cold side of a shower mixer valve), Equation 1 is solved for the useful volume of fluid. $T_c$ as determined using, for example, a thermometer 1110, is used to correct the gain and bias terms applied to the output of the thermocline sensor 104. Thermometers 1110 located at cold inlets of the vessel allow for useful volume of water delivered to end users to be determined and thermometers 1110 located at hot outlets allows monitoring of potentially unsanitary exposures to water.

The circuits comprising the thermocline sensors 104 and thermometer(s) 1140, as shown in FIGS. 11 and 12, are arranged such that the thermocline sensor 104 and thermometer(s) 1110 have a shared output terminal 1150. The shared output has no more than two or three (not shown) electrical terminals that are used to obtain an output from the thermocline sensor 104 and thermometer(s) 1110.

Figure 13:
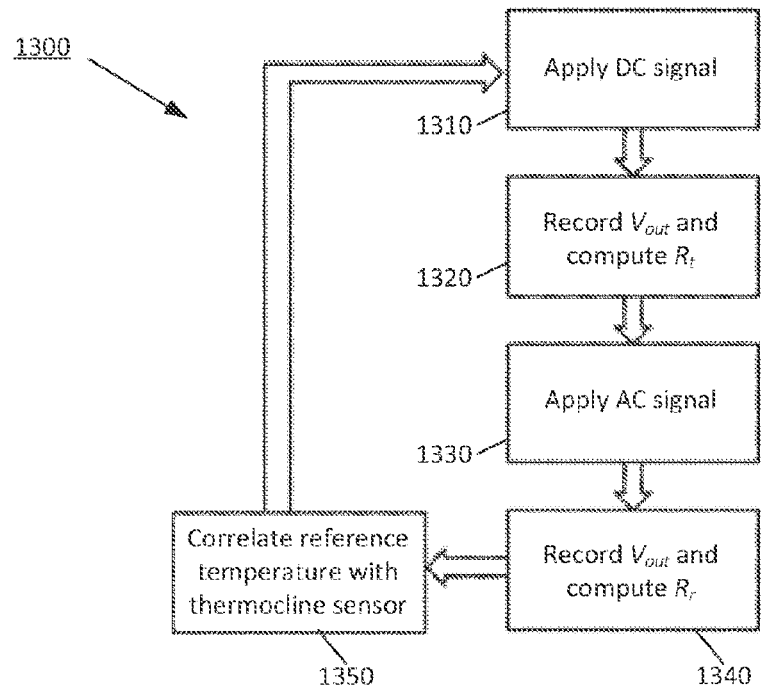
FIG. 13 shows AC and DC operation of the thermocline sensor and impedance isolated temperature sensors.

FIG. 13 shows a flow diagram of the combined thermocline sensor 104 and thermometer 1110 circuit under AC/DC operation 1300. In a first step 1310, a DC signal is applied across terminals 302, and the output signal from the circuit 1100 across output terminals 1150 is monitored. The output voltage, $V_{out}$, from output terminals 1150 is subsequently recorded and, given that $R_s$ is known and that no current flows through the thermometer 1110, the resistance across the thermocline sensor 104, $R_t$, can be computed in step 1320. In a following step 1330, an AC signal is applied across the circuit 1100 at a frequency that is far greater than the maximum anticipated value of the inverse of the zero time constant of the circuit 1100. The frequency is also selected so that it is high enough to avoid temperature related effects on the frequency response of the circuit (i.e. the thermocline sensor 104 and thermometer 1110 circuit) when sensing the reference temperature. The output voltage, $V_{out}$, is recorded and, on the basis of the change in magnitude response of the output voltage in step 1330 relative to the output voltage recorded in step 1320, $R_r$ is computed 1340. Finally, the temperature associated with the computed value of $R_r$ is correlated with $R_t$ so that the proximity of the thermocline within the vessel 106 to vessel outlet 118 and/or the remaining useable volume of water within the vessel 106 is associated with the temperature to which $R_r$ relates 1350. The process of AC/DC operation 1300 is also available to be used with circuits that have multiple thermometers 1110, as per circuit 1200. Alternatively, a DC signal is used to obtain a reading from the temperature sensor 1110 and an AC signal to obtain a signal from the thermocline sensor 104.

The thermometer 1150 is used to calibrate the output of the thermocline sensor 104, detect unsanitary exposures and, where the measurement provided by the thermometer is taken close to the vessel inlet, an indication of useful volume of fluid developed downstream of the vessel. For an array of thermometers (as shown in FIG. 12) where the output of each thermometer is available to be determined independently, the array is used in addition to the thermocline sensor 104 to determine the useful volume of fluid within the vessel developed downstream of the vessel.

Figure 14:
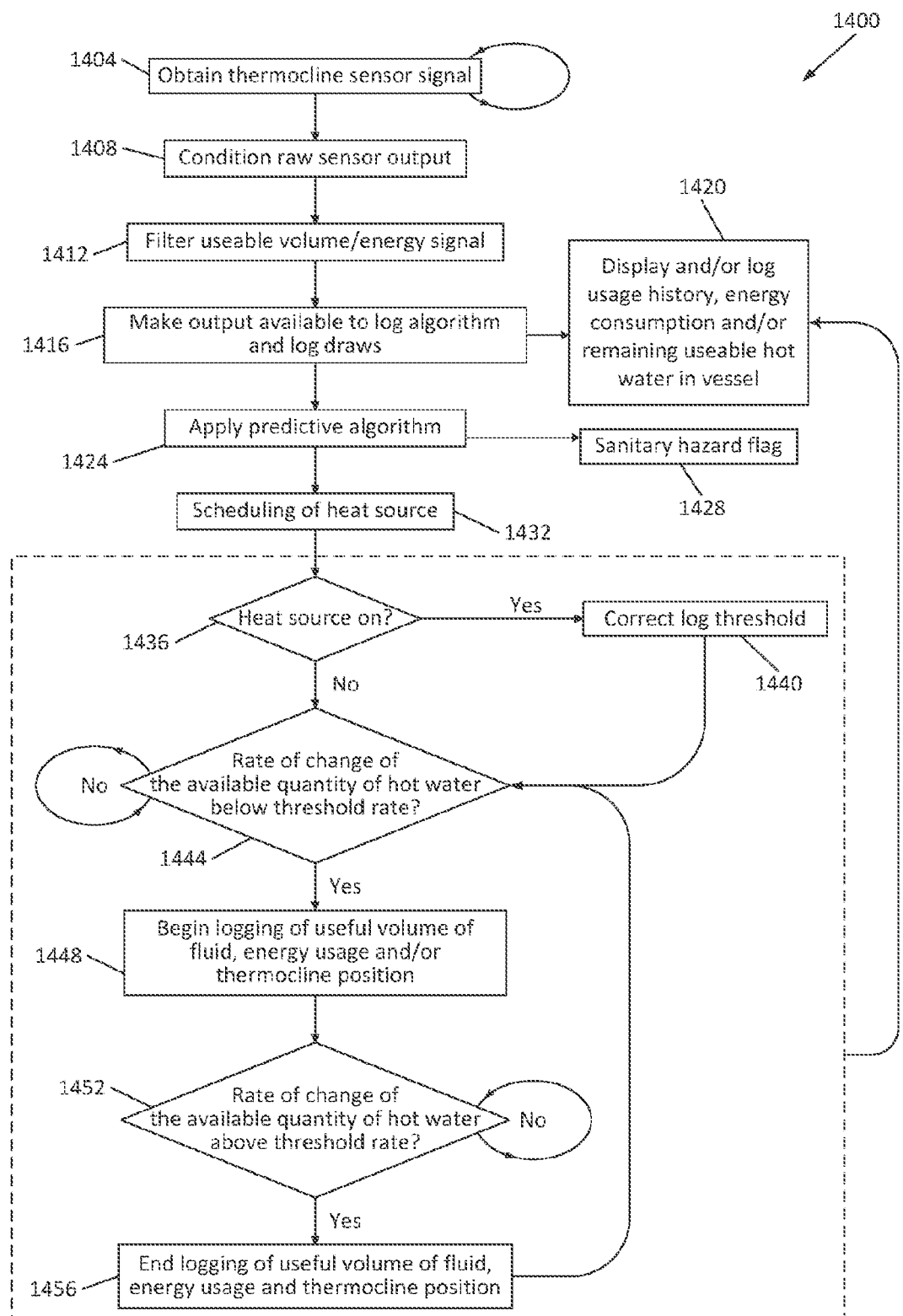
FIG. 14 is a process flow diagram showing processing of the signal from the thermocline sensor.

FIG. 14 shows signal processing of the output signal from the thermocline sensor 104 in the form of a flow diagram 1400. Once an output signal has been obtained from the thermocline sensor 104 in a first step 1404, the signal is conditioned such that the useful volume of fluid within the vessel 106 is accurately derivable, for example by using numerical integration of TED-detected temperature-dependent parameters; applying a gain and/or bias of the thermocline sensor 104; and applying a wall model and/or model fitting 1408. The signal conditioned in step 1408 is further processed in order to derive the useful volume of fluid within the vessel 106, for example by using low pass filters, Savitzky-Golay filters, moving averages and local regression 1412. The output from step 1412 is made available to an algorithm for logging draw events (a "log algorithm"), which logs draw events that result in the removal of fluid from the vessel 1416. The logged draws are displayed to the user 120 and/or recorded 1420, for example in the form of water usage history, energy consumption and/or the remaining amount of useable water within the vessel 106. A predictive model is applied to the information made available to the log algorithm 1424. For example a Markov model is used to anticipate when heating of the water within the vessel is required and/or when the water within the vessel will surpass an unsanitary threshold, as unsanitary exposures tend to coincide with large draw events (as indicated by the rate of change of the output from a thermocline sensor 104), for example during shower usage, which is of particular concern due to the added risk of inhaling contaminated water that has been aerolised.

The thermocline sensor 104 and controller 100, having the ability to determine the position of the thermocline in a stratified body of water within a vessel (and thus determine the exergy within the vessel), provide an indication of the level of the thermocline relative to the position of the vessel outlet 118 (or outlets) and therefore react (e.g. by providing a sanitary hazard flag or scheduling heating of the fluid within the vessel) in anticipation of unsanitary draw events from the vessel. The addition of at least one thermometer 1110 provides greater confidence of the temperature of fluid at a given position within the vessel, preferably at the vessel outlet 118 or inlet 121. The reliability of determining the position of the thermocline relative to a reference position is thereby improved and the sanitary conditions of water at a given position is determinable with a greater degree of certainty. The thermometer 1110 also provides a means of calibrating the output of the thermocline sensor 104 with respect to a reference temperature determined from one or more of the thermometers 1110. If the predictive model determines that user exposure to unsanitary water is likely, a sanitary hazard flag is raised 1428, either as a warning detectable by the user 120 or as a trigger for a response to prevent exposure to unsanitary water. The predictive algorithm also schedules heating of water if it anticipates that the volume of useful water is likely to be expended 1432. A determination is made at step 1436 as to whether a heat source for heating water in the vessel is currently active—if the heat source is active, then a threshold is logged and corrected 1440. A disaggregate of the volume of fluid removed from the vessel and the change in sensor output is determined at step 1440 in order to understand the user's draw activity. If a heating source is on, the threshold rate of the change in the output of the thermocline sensor associated with a draw event is corrected to recover the true recording of useful hot water drawn from the vessel. By isolating the effects of standing heat loss, and heating of the fluid due to a heating element, a more accurate indication of removal of fluid is provided. A schedule of activity of the heating element is used in addition to outputs from the controller operating the thermal source to aid decoupling of heating and draw events. Subsequently, a determination as to the rate of change of the available quantity of hot water below a threshold rate 1444 is made. Otherwise, an uncorrected log threshold is used as a parameter for step 1444. If the rate of change of the useful quantity of hot water is not below the threshold rate, the process 1444 loops; if not, logging of the useful quantity of hot water, energy usage and/or thermocline position begins 1448 and continues according to a determination of the rate of change of the available quantity of water at a useful temperature in step 1452 until this rate falls below the threshold, at which point logging of useful volume of fluid, energy usage and/or thermocline position ends 1456. Steps 1436-1456 are used to identify draw events on the basis of the changing output of a thermocline sensor or temperature array whose output is aggregated into a single measurement of useful volume of water within the vessel 106. Identification of draw events is exploited to record information on historic fluid usage, for example with an aim to inform users of their consumption habits; prime a state transition matrix within a Markov chain to predict the timing and size of future draw events for the purposes of scheduling heat sources and flag potentially unsanitary episodes or likely future instances where the outlet temperature may drop beneath a sterilizing threshold for a pathogen, such as *Legionella*. Additionally, an algorithmic procedure is provided to condition the output of the thermocline sensor 104 and track the changes in state within the vessel which occur due to draw events during operation. Steps 1436-1456 are linked the log usage display step 1420, so that the log usage can be presented or indicated to the user.

The controller 100 and/or processor 110 is able to identify distinct modes of heat loss from the vessel. Draw events from the changing output of the thermocline sensor 104 with time are identified by sudden changes detected by the thermocline sensor 104, rather than when the output of the thermocline sensor drops gradually as a result of standing heat losses.

Many domestic hot water systems have an internal heat exchanger through which hot water is extracted. In this example, knowledge of the thermocline position alone is insufficient to resolve the quantity of useable hot water in the vessel. In such cases, the temperature at the top of the vessel remains substantially constant during operation and the temperature of the outlet of the heat exchanger drops due to starvation as the thermocline transitions across the extent of the heat exchanger. A function that maps the water temperature gradient within the vessel to the availability of energy from a heat exchanger immersed within the vessel is provided. For example, for a helical coil, a mapping between the coil's height relative to the vertical position in the vessel, coil diameter and pitch are considered. An algorithm which maps the temperature profile within the vessel to the likely output from a heat exchanger for a given flow rate and inlet temperature is provided. Similarly, an algorithm used in combination with a thermal heat exchanger model and a one-dimensional or two-dimensional vessel stratification model in order to resolve the rate of change in outlet temperature for a given flow rate and inlet temperature is used, which then computes useable energy, mass or volume of hot water for a given useful temperature reference value. By providing a model of the heat exchanger the output of the thermocline sensor is available to account for the influence of the heat exchanger and more therefore allow for a more accurate determination of the useful volume of fluid.

Figure 15:
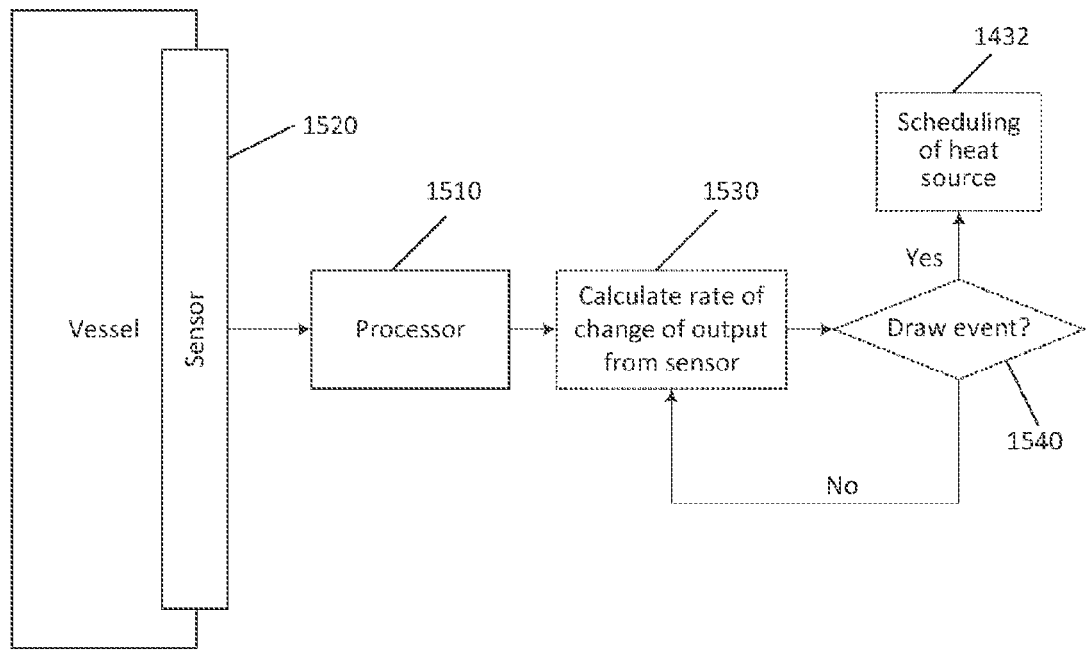
FIG. 15 shows a device for identifying draw events.

FIG. 15 shows a schematic diagram of a device, for example in the form of a processor 1510, for identifying removal of fluid from the vessel 106—a draw event. An input indicative of thermal properties of fluid within the vessel is received by the processor 1510 from a sensor 1520, for example the thermocline sensor 104. The processor identifies a draw event by considering the rate of change of the output from the sensor 1520 in a first processing step 1530. A determination is made by the processor as to whether the change in output signal is due to removal of fluid from the vessel or due to static heat loss from the vessel 1540; if the determination indicates the former cause, the processor outputs an instruction to induce dispatch of energy to a heat source to manipulate the temperature of the fluid within the vessel 1432.

Figure 16:
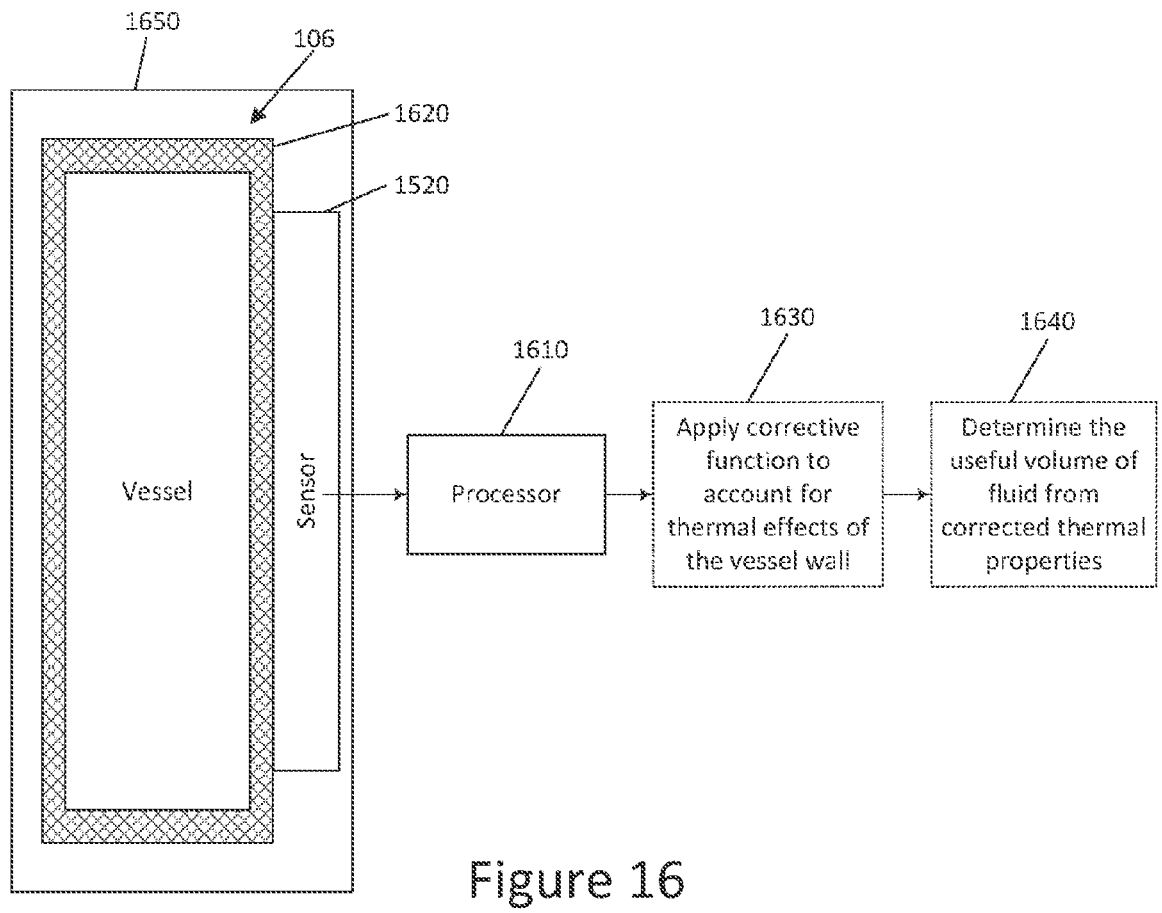
FIG. 16 shows a device for correcting for thermal effects of a vessel wall.

FIG. 16 shows a schematic diagram of a device, for example in the form of a processor 1610, which receives an output from a sensor 1520 that determines thermal properties of a fluid within the vessel through a conductive barrier, such as the vessel wall 1620. The processor applies a corrective function to the signal received from the sensor 1520 in order to account for the thermal effects of the vessel wall and indicate more accurately the thermal properties of the fluid within the vessel 1630. The useful volume of fluid within the vessel is therefore determined 1640 more accurately using a sensor that measures thermal properties of the fluid through a conductive barrier by using the adjusted measure of the thermal properties of the fluid by the processor 1610. The vessel 106 and sensor 1520 are shown enveloped by a layer of thermal insulation 1650.

The vessel 106 described with reference to FIG. 1 is for example an immersion heating tank or a similar installation, with an inlet 121 and an outlet 118 in fluid communication with the vessel content. The vessel can take other forms, for example a heat exchange vessel or a heat store vessel where a fluid conduit (with an inlet and outlet) is in thermal communication, but not fluid communication, with the vessel content; or a vessel such as a kettle where the fluid inlet and outlet are combined in a single aperture. Common to the vessels is a fluid with a temperature profile extending between a first region and a second region of the vessel, typically due to a localised thermal source or drain, and/or thermal stratification in the vessel.

In one example, the thermocline sensor 104 is integrated onto a flexible strip, such as a strip of composite copper, polymer composite (e.g. Espanex or Kapton) and any of the aforementioned circuitry is available to be printed onto the flexible strip surface prior to etching in a ferric chloride bath. For easy retrofit of the thermocline sensor, a portion of the outer insulation of the vessel 108, as is commonly present, is removed and the sensor located in the recess formed from the removal of the insulation. The circuitry comprising the thermocline sensor 104 is arranged such that an adhesive layer is appended to the vessel 108 wall surface, thereby allowing a layer of flexible polymer above the adhesive layer to be in thermal contact with the vessel wall. Above the flexible polymer layer, a layer of copper and/or printed circuit board trace is present with a layer of electrical components is provided above therein. An outer insulation layer on the thermocline sensor arrangement is placed as a final layer. It is therefore envisaged that thermocline sensors 104 composed on reels of flexible strips of adhesive tape are manufactured by a continuous method of production. A kit of parts for easy retrofit onto a vessel is therefore available.

In one example the PTC or NTC elements used in the thermocline sensor 104 have a non-linear response (e.g. as per a thermistor made of Barium Titanate), in particular around the Curie transition temperature. The Curie transition temperature is used to provide an integral limit that differentiates between useful and non-useful energy. Advantageously the response of a PTC resistor will occur only above a certain threshold thereby introducing an inherent threshold for judging a useful temperature.

It will be understood that the present invention has been described above purely by way of example, and modifications of detail can be made within the scope of the invention.

Each feature disclosed in the description, and (where appropriate) the claims and drawings may be provided independently or in any appropriate combination.

Reference numerals appearing in the claims are by way of illustration only and shall have no limiting effect on the scope of the claims.

The invention claimed is:

1. A sensor for measuring temperature of a fluid at different regions within a vessel, the sensor comprising:
   an array of elements coupled together between an input and an output, each element having a temperature-dependent parameter;
   wherein the array of elements is extendable along the vessel for measuring a temperature profile of the fluid within the vessel, with the input coupled to a driving source for driving the sensors and the output coupled to a detector for measuring an aggregate of the temperature-dependent parameter from the array of elements, the aggregate being indicative of a quantity of useful fluid in the vessel, useful fluid being fluid having a temperature above a threshold temperature; and
   wherein at least one of the elements in the array comprises a fixed value resistor connected in parallel with a Positive Temperature Coefficient thermistor with a Curie transition temperature at or near a temperature of interest or a Negative Temperature Coefficient thermistor with a Curie transition temperature at or near a temperature of interest.

2. The sensor according to claim 1, wherein the array comprises a substrate that can be cut to length to determine the number of elements within the array.

3. The sensor according to claim 2, wherein the substrate comprises adhesive tape.

4. The sensor according to claim 1, wherein the elements of the array are non-uniformly distributed along the length of the array.

5. The sensor according to claim 1 arranged to provide output relating to a thermal property of the fluid within a vessel, and a processor arranged to identify removal of the fluid from the vessel in dependence on a rate of change of the output from the sensor and a predetermined threshold value of the output, whereby to identify removal of fluid from a vessel.

6. The sensor according to claim 1, for determining a thermal property of a fluid within a vessel, wherein the sensor is arranged to be fitted onto an exterior wall of the vessel; and
   a processor for receiving the output from the sensor and adjusting the output according to thermal properties of the wall of the vessel, whereby to measure temperature of a fluid within a vessel.

7. The sensor according to claim 1, for determining a useful volume of a fluid within a vessel, wherein the sensor is arranged to be fitted onto an exterior wall of the vessel; and
   a processor for receiving an output from the sensor and adjusting the output from the sensor in dependence upon changes induced in the fluid by a thermal source, whereby to measure temperature of a fluid within a vessel.

8. A vessel for holding a fluid, the vessel comprising a sensor according to claim 1.

9. The sensor according to claim 1, wherein at least two adjacent elements of the array comprise a Positive Temperature Coefficient thermistor with a Curie transition temperature at or near a temperature of interest and a Negative Temperature Coefficient thermistor with a Curie transition temperature at or near a temperature of interest.

10. The sensor according to claim 1, wherein at least one of the elements of the array comprises a Positive Temperature Coefficient thermistor connected in parallel with a Negative Temperature Coefficient thermistor and in series thereto a fixed value thermistor, and wherein at least one of the Positive Temperature Coefficient thermistor and Negative Temperature Coefficient thermistor is a non-linear thermistor.

11. The sensor according to claim 1, wherein at least one of the elements of the array is configured such that the temperature-dependence of the temperature-dependent parameter is at or near a maximum or minimum at or near a temperature that is a threshold temperature between a useful temperature of the fluid and a non-useful temperature of the fluid.

12. The sensor according to claim 1, wherein the parameter is resistance, impedance, inductance and/or capacitance.

13. The sensor according to claim 1, wherein the elements of the array are coupled together in series or in parallel.

14. The sensor according to claim 1, wherein the Positive Temperature Coefficient thermistor and/or Negative Temperature Coefficient thermistor is a non-linear thermistor.

15. A sensing arrangement comprising:
   a sensor comprising an array of elements coupled together between an input and an output, each element having a temperature-dependent parameter, wherein the array of elements is extendable along the vessel for measuring the temperature profile of the fluid within the vessel, with the input coupled to a driving source for driving the sensors and the output coupled to a detector for measuring an aggregate of the temperature-dependent parameter from the array of elements, the aggregate being indicative of a quantity of useful fluid in the vessel, useful fluid being fluid having a temperature above a threshold temperature, wherein at least one of the elements in the array comprises a fixed value resistor connected in parallel with a Positive Temperature Coefficient thermistor with a Curie transition temperature at or near a temperature of interest or a Negative Temperature Coefficient thermistor with a Curie transition temperature at or near a temperature of interest; and
   at least one thermometer, the sensor and said at least one thermometer having a shared output.

16. The sensing arrangement according to claim 15, wherein the sensor and said at least one thermometer are coupled together to provide only two output connectors for the shared output, and/or
   wherein the sensor and said at least one thermometer are arranged in parallel, and/or further comprising means for measuring an output from the thermometer separately to the output from the sensor, and/or wherein the thermometer is arranged to monitor temperature adjacent the vessel outlet or inlet to detect when fluid is at an unsanitary temperature.

17. The sensing arrangement according to claim 15 in combination with a controller arranged to process the shared output from the sensing arrangement, wherein the sensing arrangement and/or controller is arranged to determine signals from the sensor and at least one thermometer separately and to compute the useful quantity of thermal energy within a vessel containing a fluid.

18. The sensing arrangement according to claim 17, wherein the combination is arranged to determine signals from the sensor and thermometer separately by impedance isolation of the thermometer.

19. A fluid temperature controller comprising:

a first input for receiving a first signal indicating a measurement of an aggregate of a temperature-dependent parameter from a sensor deployed within or adjacent a vessel containing a fluid having a temperature profile, the sensor comprising an array of elements coupled together between an input and an output, each element having a temperature-dependent parameter, wherein the array of elements is extendable along the vessel for measuring the temperature profile of the fluid within the vessel, with the input coupled to a driving source for driving the sensors and the output coupled to a detector for measuring an aggregate of the temperature-dependent parameter from the array of elements, the aggregate being indicative of a quantity of useful fluid in the vessel, useful fluid being fluid having a temperature above a threshold temperature, wherein at least one of the elements in the array comprises a fixed value resistor connected in parallel with a Positive Temperature Coefficient thermistor with a Curie transition temperature at or near a temperature of interest or a Negative Temperature Coefficient thermistor with a Curie transition temperature at or near a temperature of interest;

a second input for receiving a second signal indicating a temperature of the fluid in the vessel; and a processor configured to calculate a total thermal energy of the fluid in the vessel based on the first and second signals.

20. The fluid temperature controller according to claim 19, wherein the processor is further configured to determine a volume of useful fluid in the vessel based on the first and second signals and a predetermined threshold temperature between a useful temperature of the fluid and a non-useful temperature of the fluid, and/or wherein the processor is further configured to provide an output control signal for controlling a thermal source that changes temperature of the fluid in the vessel, and/or wherein the processor is configured to operate in dependence upon the number of array elements and/or array element spacing along the length of the sensor, and/or further comprising a network stress monitor, the network stress monitor being arranged to receive data from a network operator and modify the output control signal to the thermal source in dependence of the data received from the network operator.

\* \* \* \* \*